(12) United States Patent
Clark

(10) Patent No.: US 8,858,594 B2
(45) Date of Patent: Oct. 14, 2014

(54) CURVED CLOSURE DEVICE

(75) Inventor: Ian J. Clark, West Bloomfield, MI (US)

(73) Assignee: Abbott Laboratories, Abbott Park, IL (US)

( * ) Notice: Subject to any disclaimer, the term of this patent is extended or adjusted under 35 U.S.C. 154(b) by 558 days.

(21) Appl. No.: 12/642,319

(22) Filed: Dec. 18, 2009

(65) Prior Publication Data

US 2010/0168790 A1 Jul. 1, 2010

Related U.S. Application Data

(63) Continuation-in-part of application No. 12/481,377, filed on Jun. 9, 2009, now Pat. No. 8,323,312.

(60) Provisional application No. 61/141,597, filed on Dec. 30, 2008, provisional application No. 61/139,995, filed on Dec. 22, 2008.

(51) Int. Cl.
| | | |
|---|---|---|
| *A61B 17/08* | (2006.01) | |
| *A61B 17/00* | (2006.01) | |
| *A61B 17/064* | (2006.01) | |
| *A61B 17/068* | (2006.01) | |
| *A61B 19/00* | (2006.01) | |

(52) U.S. Cl.
CPC ... *A61B 17/0057* (2013.01); *A61B 2017/00637* (2013.01); *A61B 2017/00668* (2013.01); *A61B 2017/0641* (2013.01); *A61B 2017/00867* (2013.01); *A61B 17/068* (2013.01); *A61B 19/54* (2013.01); *A61B 17/064* (2013.01); *A61B 2017/00986* (2013.01)
USPC .......................... 606/216; 606/155; 606/221

(58) Field of Classification Search
USPC ............... 606/139, 151, 153, 155, 157, 158, 606/213–217, 142, 221; 623/23.72
See application file for complete search history.

(56) References Cited

U.S. PATENT DOCUMENTS

| | | |
|---|---|---|
| 287,046 A | 10/1883 | Norton |
| 438,400 A | 10/1890 | Brennen |
| 556,082 A | 3/1896 | Boeddinghaus |

(Continued)

FOREIGN PATENT DOCUMENTS

| | | |
|---|---|---|
| AU | 2003297432 | 7/2004 |
| CA | 2 339 060 | 2/2000 |

(Continued)

OTHER PUBLICATIONS

U.S. Appl. No. 12/338,977, Jan. 19, 2012, Office Action.

(Continued)

*Primary Examiner* — Thomas McEvoy
*Assistant Examiner* — Rachel S Papeika
(74) *Attorney, Agent, or Firm* — Workman Nydegger; Randy Shen

(57) ABSTRACT

Devices and methods are disclosed herein for a closure device. A closure device includes a body movable from a pre-deployed configuration towards a deployed configuration, a plurality of tissue-engaging portions extending from the body. At least two of the tissue-engaging portions are separated by a first distance in the deployed configuration and a second distance in the pre-deployed configuration in which the first distance is smaller than the second distance. The closure device also includes a plurality of device capture features secured to the body. The device capture features are configured to move the tissue-engaging portions to a separation greater than the first distance.

19 Claims, 16 Drawing Sheets

(56) References Cited

U.S. PATENT DOCUMENTS

| | | |
|---|---|---|
| 1,088,393 A | 2/1914 | Backus |
| 1,242,139 A | 10/1917 | Callahan |
| 1,331,401 A | 2/1920 | Summers |
| 1,480,935 A | 1/1924 | Gleason |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood |
| 3,604,425 A | 9/1971 | Le Roy |
| 3,618,447 A | 11/1971 | Goins |
| 3,677,243 A | 7/1972 | Nerz |
| 3,682,180 A | 8/1972 | McFarlane |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |

(56) References Cited

U.S. PATENT DOCUMENTS

| | | |
|---|---|---|
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Valez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs Van De Moer et al. |
| 5,626,614 A | 5/1997 | Hart |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |

(56) References Cited

U.S. PATENT DOCUMENTS

| | | |
|---|---|---|
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,167 A | 12/1998 | Dwyer et al. |
| 5,845,657 A | 12/1998 | Carberry et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,161 A | 11/1999 | Kirsch et al. |
| 5,976,174 A | 11/1999 | Ruiz |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |

(56) References Cited

U.S. PATENT DOCUMENTS

| | | |
|---|---|---|
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |

(56) References Cited

U.S. PATENT DOCUMENTS

| | | |
|---|---|---|
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walburg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,780,696 B2 | 8/2010 | Daniel et al. |
| 7,799,042 B2 | 9/2010 | Williamson, IV et al. |
| 7,819,895 B2 | 10/2010 | Ginn et al. |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelöv |
| 8,226,666 B2 | 7/2012 | Zarbatany et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1* | 3/2002 | Gifford et al. .......... 606/153 |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0062104 A1 | 5/2002 | Ashby et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2004/0009205 A1 | 1/2004 | Sawhney |
| 2004/0009289 A1 | 1/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |

(56) References Cited

U.S. PATENT DOCUMENTS

| | | |
|---|---|---|
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0256532 A1* | 11/2005 | Nayak et al. .................. 606/151 |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1* | 12/2007 | Carley et al. .................. 606/142 |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0066163 A1 | 3/2011 | Cho et al. |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Kariniemi et al. |
| 2012/0245626 A1 | 9/2012 | Ellingwood et al. |

(56) References Cited

U.S. PATENT DOCUMENTS

| | | | |
|---|---|---|---|
| 2012/0310261 A1 | 12/2012 | Cummins et al. | |
| 2013/0006274 A1 | 1/2013 | Walberg et al. | |
| 2013/0338708 A1 | 12/2013 | Cummins et al. | |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 12/684,569, Jan. 27, 2012, Office Action.
U.S. Appl. No. 13/017,636, filed Jan. 31, 2011, Carley et al.
U.S. Appl. No. 10/616,832, Jan. 26, 2011, Issue Notification.
U.S. Appl. No. 11/152,562, Jan. 26, 2011, Issue Notification.
U.S. Appl. No. 13/030,922, filed Feb. 18, 2011, Cummins.
U.S. Appl. No. 10/356,214, Feb. 23, 2011, Issue Notification.
U.S. Appl. No. 13/026,989, filed Feb. 14, 2011, Cummins.
U.S. Appl. No. 10/264,306, Feb. 16, 2011, Issue Notification.

(56) References Cited

OTHER PUBLICATIONS

U.S. Appl. No. 11/767,818, Feb. 16, 2011, Office Action.
U.S. Appl. No. 11/958,281, Mar. 10, 2011, Office Action.
U.S. Appl. No. 11/532,576, Mar. 16, 2011, Issue Notification.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Restriction Requirement.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 11/396,731, Mar. 22, 2011, Office Action.
U.S. Appl. No. 11/427,297, Mar. 21, 2011, Office Action.
U.S. Appl. No. 12/113,851, Mar. 29, 2012, Office Action.
U.S. Appl. No. 12/403,277, Apr. 3, 2012, Office Action.
U.S. Appl. No. 12/122,603, Apr. 22, 2011, Office Action.
U.S. Appl. No. 12/113,851, Apr. 27, 2011, Office Action.
U.S. Appl. No. 12/481,377, Apr. 28, 2011, Office Action.
U.S. Appl. No. 13/308,227, filed Nov. 30, 2011, Yibarren.
U.S. Appl. No. 11/390,586, May 3, 2012, Notice of Allowance.
U.S. Appl. No. 12/114,091, Apr. 5, 2012, Office Action.
U.S. Appl. No. 12/684,542, Apr. 16, 2012, Office Action.
U.S. Appl. No. 12/688,065, Apr. 26, 2012, Office Action.
U.S. Appl. No. 12/897,358, May 2, 2012, Issue Notification.
U.S. Appl. No. 60/793,444, filed Apr. 20, 2006, Jones et al.
U.S. Appl. No. 61/141,597, filed Dec. 30, 2008, Clark.
U.S. Appl. No. 11/344,891, May 7, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 12/114,031, May 11, 2011, Office Action.
U.S. Appl. No. 12/143,020, May 11, 2011, Office Action.
U.S. Appl. No. 12/135,858, Jul. 13, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 11/396,731, Sep. 1, 2011, Office Action.
U.S. Appl. No. 12/393,877, Sep. 29, 2011, Office Action.
U.S. Appl. No. 12/122,603, Sep. 23, 2011, Office Action.
U.S. Appl. No. 11/767,818, Feb. 3, 2012, Notice of Allowance.
U.S. Appl. No. 12/684,542, Jan. 30, 2012, Restriction Requirement.
U.S. Appl. No. 12/941,809, Jan. 30, 2012, Office Action.
U.S. Appl. No. 12/966,923, Feb. 3, 2012, Notice of Allowance.
U.S. Appl. No. 10/667,144, Oct. 28, 2011, Notice of Allowance.
U.S. Appl. No. 11/675,462, Dec. 22, 2011, Notice of Allowance.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Restriction Requirement.
U.S. Appl. No. 12/684,470, Dec. 20, 2011, Restriction Requirement.
U.S. Appl. No. 12/684,562, Dec. 28, 2011, Restriction Requirement.
U.S. Appl. No. 12/684,569, Dec. 20, 2011, Restriction Requirement.
U.S. Appl. No. 12/897,358, Jan. 12, 2012, Notice of Allowance.
U.S. Appl. No. 12/941,809, Dec. 13, 2011, Restriction Requirement.
U.S. Appl. No. 12/945,646, Oct. 26, 2011, Office Action.
U.S. Appl. No. 12/955,859, Dec. 15, 2011, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/143,020, Feb. 23, 2012, Notice of Allowance.
U.S. Appl. No. 12/548,274, Mar. 2, 2012, Office Action.
U.S. Appl. No. 12/608,769, Feb. 10, 2012, Office Action.
U.S. Appl. No. 12/684,400, Feb. 13, 2012, Office Action.
U.S. Appl. No. 12/684,562, Feb. 16, 2012, Office Action.
U.S. Appl. No. 12/724,304, Feb. 10, 2012, Office Action.
U.S. Appl. No. 12/945,646, Feb. 21, 2012, Notice of Allowance.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/961,331, filed Dec. 6, 2010, Voss.
U.S. Appl. No. 12/945,646, filed Nov. 12, 2010, Carley et al.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 10/006,400, Aug. 2, 2010, Notice of Allowance.
U.S. Appl. No. 10/147,774, Jun. 8, 2010, Office Action.
U.S. Appl. No. 10/147,774, Dec. 2, 2010, Notice of Allowance.
U.S. Appl. No. 10/264,306, Jun. 15, 2010, Office Action.
U.S. Appl. No. 10/264,306, Oct. 29, 2010, Notice of Allowance.
U.S. Appl. No. 10/356,214, Sep. 3, 2010, Notice of Allowance.
U.S. Appl. No. 10/435,104, Jul. 23, 2009, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/435,104, Jan. 12, 2011, Issue Notification.
U.S. Appl. No. 10/517,004, Aug. 3, 2010, Notice of Allowance.
U.S. Appl. No. 10/517,004, Nov. 23, 2010, Issue Notification.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Sep. 20, 2010, Notice of Allowance.
U.S. Appl. No. 10/638,115, Aug. 13, 2010, Notice of Allowance.
U.S. Appl. No. 10/638,115, Dec. 22, 2010, Issue Notification.
U.S. Appl. No. 10/667,144, Jun. 22, 2010, Office Action.
U.S. Appl. No. 10/669,313, Oct. 31, 2005, Office Action.
U.S. Appl. No. 10/682,459, Oct. 12, 2010, Office Action.
U.S. Appl. No. 10/787,073, Aug. 25, 2010, Notice of Allowance.
U.S. Appl. No. 10/787,073, Sep. 15, 2010, Issue Notification.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Jul. 6, 2010, Office Action.
U.S. Appl. No. 11/113,549, Jan. 4, 2011, Office Action.
U.S. Appl. No. 11/152,562, Sep. 16, 2010, Notice of Allowance.
U.S. Appl. No. 11/198,811, Jun. 29, 2010, Notice of Allowance.
U.S. Appl. No. 11/198,811, Oct. 20, 2010, Issue Notification.
U.S. Appl. No. 11/390,586, Jul. 6, 2010, Office Action.
U.S. Appl. No. 11/396,731, Jun. 29, 2010, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/427,297, Sep. 15, 2010, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/532,576, Oct. 13, 2010, Notice of Allowance.
U.S. Appl. No. 11/675,462, Aug. 31, 2010, Office Action.
U.S. Appl. No. 11/757,108, Nov. 25, 2009, Office Action.
U.S. Appl. No. 11/767,818, Sep. 30, 2010, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,295, May 25, 2010, Office Action.
U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Oct. 25, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,091, Oct. 27, 2010, Office Action.
U.S. Appl. No. 12/114,091, Dec. 17, 2010, Office Action.
U.S. Appl. No. 12/402,398, May 20, 2010, Office Action.
U.S. Appl. No. 12/402,398, Jan. 24, 2011, Office Action.
U.S. Appl. No. 12/403,256, Aug. 19, 2010, Notice of Allowance.
U.S. Appl. No. 12/403,256, Nov. 23, 2010, Issue Notification.
U.S. Appl. No. 12/403,277, Jul. 8, 2010, Office Action.
U.S. Appl. No. 12/403,277, Oct. 12, 2010, Office Action.
U.S. Appl. No. 12/945,646, Jan. 20, 2011, Office Action.
U.S. Appl. No. 13/039,087, filed Mar. 2, 2011, Palermo et al.
U.S. Appl. No. 11/852,190, Mar. 2, 2011, Office Action.
U.S. Appl. No. 12/122,603, Mar. 3, 2011, Office Action.
U.S. Appl. No. 10/147,774, Apr. 6, 2011, Issue Notification.
U.S. Appl. No. 10/682,459, Apr. 1, 2011, Notice of Allowance.
U.S. Appl. No. 12/403,277, Mar. 31, 2011, Office Action.
U.S. Appl. No. 60/696,069, filed Jul. 1, 2005, Pantages et al.

(56) References Cited

OTHER PUBLICATIONS

U.S. Appl. No. 60/693,531, filed Jun. 24, 2005, Carly.
U.S. Appl. No. 60/843,325, filed Sep. 8, 2006, Carly.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/139,995, filed Dec. 22, 2008, Clark.
U.S. Appl. No. 12/113,092, filed Apr. 30, 2008, Ginn et al.
U.S. Appl. No. 12/393,877, filed Feb. 26, 2009, Ellingwood et al.
U.S. Appl. No. 12/481,377, filed Jun. 9, 2009, Clark.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.

OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma—Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, Md, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, Nov. 6, 2000, Notice of Allowance.
U.S. Appl. No. 09/478,179, Feb. 15, 2001, Issue Notification.

(56) References Cited

OTHER PUBLICATIONS

U.S. Appl. No. 09/546,998, May 6, 2002, Notice of Allowance.
U.S. Appl. No. 09/546,998, Sep. 19, 2002, Issue Notification.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/610,238, May 3, 2002, Issue Notification.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/680,837, Sep. 11, 2003, Issue Notification.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,178, Mar. 25, 2004, Issue Notification.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/764,813, Aug. 6, 2001, Issue Notification.
U.S. Appl. No. 09/933,299, Feb. 26, 2003, Office Action.
U.S. Appl. No. 09/933,299, Jun. 16, 2003, Notice of Allowance.
U.S. Appl. No. 09/933,299, Sep. 25, 2003, Issue Notification.
U.S. Appl. No. 09/948,813, Jan. 31, 2003, Notice of Allowance.
U.S. Appl. No. 09/948,813, Jun. 5, 2003, Issue Notification.
U.S. Appl. No. 09/949,398, Mar. 4, 2003, Office Action.
U.S. Appl. No. 09/949,398, Jul. 28, 2003, Notice of Allowance.
U.S. Appl. No. 09/949,398, Dec. 11, 2003, Issue Notification.
U.S. Appl. No. 09/949,438, Dec. 17, 2002, Office Action.
U.S. Appl. No. 09/949,438, Apr. 21, 2003, Notice of Allowance.
U.S. Appl. No. 09/949,438, Aug. 21, 2003, Issue Notification.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/081,717, Sep. 29, 2003, Notice of Allowance.
U.S. Appl. No. 10/081,717, Feb. 5, 2004, Issue Notification.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,725, May 27, 2004, Issue Notification.
U.S. Appl. No. 10/081,726, Apr. 11, 2003, Notice of Allowance.
U.S. Appl. No. 10/081,726, Jun. 9, 2003, Office Action.
U.S. Appl. No. 10/081,726, Sep. 4, 2003, Issue Notification.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, May 26, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/335,075, Apr. 11, 2007, Issue Notification.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Office Action.
U.S. Appl. No. 10/435,104, Feb. 15, 2006, Issue Notification.
U.S. Appl. No. 10/435,104, May 16, 2006, Office Action.
U.S. Appl. No. 10/435,104, Dec. 28, 2006, Notice of Allowance.
U.S. Appl. No. 10/435,104, May 23, 2007, Issue Notification.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jan. 20, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,067, Dec. 27, 2006, Issue Notification.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/541,083, Sep. 30, 2009, Notice of Allowance.
U.S. Appl. No. 10/616,832, Sep. 17, 2008, Office Action.

(56) References Cited

OTHER PUBLICATIONS

U.S. Appl. No. 10/616,832, Jul. 21, 2009, Office Action.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/617,090, Feb. 1, 2006, Issue Notification.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/669,313, Nov. 15, 2006, Issue Notification.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/390,586, Jun. 24, 2009, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/675,462, Dec. 10, 2009, Office Action.
U.S. Appl. No. 11/744,089, Nov. 26, 2008, Office Action.
U.S. Appl. No. 11/744,089, Aug. 14, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/958,295, Aug. 27, 2009, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 12/106,937, Mar. 30, 2009, Office Action.
U.S. Appl. No. 12/106,937, Nov. 18, 2009, Office Action.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/113,851, Apr. 27, 2010, Office Action.
U.S. Appl. No. 12/402,398, Mar. 9, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 13/112,618, filed May 20, 2011, Gianotti et al.
U.S. Appl. No. 13/112,631, filed May 20, 2011, Voss.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 13/525,718, filed Jun. 18, 2012, Carley et al.
U.S. Appl. No. 12/393,877, May 21, 2012, Office Action.
U.S. Appl. No. 12/608,773, Jun. 7, 2012, Office Action.
U.S. Appl. No. 12/684,400, May 9, 2012, Office Action.
U.S. Appl. No. 12/941,809, Jun. 1, 2012, Office Action.
U.S. Appl. No. 13/026,989, Jun. 8, 2012, Office Action.
U.S. Appl. No. 12/481,377, Jun. 21, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 13/039,087, Jul. 17, 2012, Office Action.
U.S. Appl. No. 12/955,859, Jul. 21, 2011, Office Action.
U.S. Appl. No. 10/682,459, Aug. 10, 2011, Issue Notification.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 13/026,989, Sep. 16, 2011, Office Action.

(56) References Cited

OTHER PUBLICATIONS

U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 11/675,462, Aug. 15, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/608,773, Jul. 20, 2012, Office Action.
U.S. Appl. No. 12/684,562, Aug. 21, 2012, Office Action.
U.S. Appl. No. 12/684,569, Jul. 30, 2012, Office Action.
U.S. Appl. No. 12/850,242, Aug. 6, 2012, Office Action.
U.S. Appl. No. 12/955,859, Aug. 6, 2012, Office Action.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.
U.S. Appl. No. 12/106,928, Jun. 28, 2013, Office Action.
U.S. Appl. No. 12/106,937, Jun. 28, 2013, Office Action.
U.S. Appl. No. 12/941,809, Jul. 3, 2013, Office Action.
U.S. Appl. No. 12/961,331, Jul. 3, 2013, Office Action.
U.S. Appl. No. 11/396,141, Aug. 21, 2013, Office Action.
U.S. Appl. No. 13/490,143, Aug. 21, 2013, Issue Notification.
U.S. Appl. No. 13/153,594, May 29, 2013, Office Action.
U.S. Appl. No. 13/791,829, May 29, 2013, Office Action.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 11/344,891, Jan. 22, 2013, Notice of Allowance.
U.S. Appl. No. 12/114,091, Nov. 8, 2012, Office Action.
U.S. Appl. No. 12/338,977, Nov. 28, 2012, Office Action.
U.S. Appl. No. 12/402,398, Sep. 20, 2012, Office Action.
U.S. Appl. No. 12/403,277, Nov. 5, 2012, Office Action.
U.S. Appl. No. 12/548,274, Sep. 10, 2012, Office Action.
U.S. Appl. No. 12/608,769, Aug. 22, 2012, Office Action.
U.S. Appl. No. 12/608,769, Nov. 5, 2012, Notice of Allowance.
U.S. Appl. No. 12/608,773, Jan. 7, 2013, Office Action.
U.S. Appl. No. 12/684,400, Oct. 16, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/688,065, Oct. 12, 2012, Office Action.
U.S. Appl. No. 12/848,642, Sep. 20, 2012, Restriction Requirement.
U.S. Appl. No. 12/848,642, Nov. 9, 2012, Office Action.
U.S. Appl. No. 12/850,242, Oct. 17, 2012, Office Action.
U.S. Appl. No. 12/961,331, Dec. 4, 2012, Restriction Requirement.
U.S. Appl. No. 12/987,792, Sep. 17, 2012, Office Action.
U.S. Appl. No. 13/030,922, Dec. 18, 2012, Restriction Requirement.
U.S. Appl. No. 13/039,087, Nov. 6, 2012, Notice of Allowance.
U.S. Appl. No. 13/490,143, Jan. 4, 2013, Restriction Requirement.
U.S. Appl. No. 13/615,547, Jan. 18, 2013, Office Action.
U.S. Appl. No. 12/402,398, Mar. 13, 2013, Notice of Allowance.
U.S. Appl. No. 12/961,331, Feb. 1, 2013, Office Action.
U.S. Appl. No. 13/030,922, Jan. 31, 2013, Office Action.
U.S. Appl. No. 13/153,594, Jan. 29, 2013, Office Action.
U.S. Appl. No. 13/488,233, Feb. 5, 2013, Notice of Allowance.
U.S. Appl. No. 10/908,721, Jul. 18, 2013, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 11/427,309, Jun. 7, 2013, Notice of Allowance.
U.S. Appl. No. 12/338,977, Jun. 19, 2013, Office Action.
U.S. Appl. No. 13/112,618, Jun. 7, 2013, Office Action.
U.S. Appl. No. 10/786,444, Jul. 11, 2013, Notice of Allowance.
U.S. Appl. No. 11/532,325, Jul. 17, 2013, Office Action.
U.S. Appl. No. 13/030,922, Jul. 18, 2013, Office Action.
U.S. Appl. No. 13/525,839, Jul. 15, 2013, Notice of Allowance.
U.S. Appl. No. 13/615,547, Jul. 10, 2013, Issue Notification.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 13/026,989, Aug. 23, 2013, Office Action.
U.S. Appl. No. 13/308,227, Sep. 11, 2013, Office Action.
U.S. Appl. No. 14/246,926, filed Apr. 7, 2014, Carley et al.
U.S. Appl. No. 14/246,973, filed Apr. 1, 2014, Carley et al.
Turn—macmillandictionary.com/dictionary.american/turn.
Turn—Merriam-webster.com/dictionary/turn.
U.S. Appl. No. 11/113,549, Mar. 14, 2014, Notice of Allowance.
U.S. Appl. No. 11/396,141, Nov. 4, 2013, Notice of Allowance.
U.S. Appl. No. 11/396,141, Mar. 19, 2014, Issue Notification.
U.S. Appl. No. 11/411,925, Oct. 1, 2013, Office Action.
U.S. Appl. No. 11/411,925, Feb. 5, 2014, Notice of Allowance.
U.S. Appl. No. 11/455,993, Jan. 29, 2014, Office Action.
U.S. Appl. No. 11/532,325, Dec. 2, 2013, Office Action.
U.S. Appl. No. 11/674,930, Apr. 3, 2014, Notice of Allowance.
U.S. Appl. No. 11/852,190, Nov. 26, 2013, Office Action.
U.S. Appl. No. 11/852,190, Feb. 12, 2014, Notice of Allowance.
U.S. Appl. No. 12/106,928, Dec. 2, 2013, Office Action.
U.S. Appl. No. 12/106,928, Mar. 25, 2014, Advisory Action.
U.S. Appl. No. 12/106,937, Jan. 22, 2014, Office Action.
U.S. Appl. No. 12/113,851, Mar. 17, 2014, Office Action.
U.S. Appl. No. 12/114,031, Mar. 10, 2014, Office Action.
U.S. Appl. No. 12/122,603, Nov. 20, 2013, Office Action.
U.S. Appl. No. 12/403,277, Jan. 27, 2014, Office Action.
U.S. Appl. No. 12/688,065, Oct. 18, 2013, Office Action.
U.S. Appl. No. 12/688,065, Apr. 8, 2014, Office Action.
U.S. Appl. No. 12/848,642, Feb. 3, 2014, Notice of Allowance.
U.S. Appl. No. 12/941,809, Nov. 8, 2013, Office Action.
U.S. Appl. No. 12/941,809, Feb. 3, 2014, Notice of Allowance.
U.S. Appl. No. 12/961,331, Sep. 20, 2013, Advisory Action.
U.S. Appl. No. 12/987,792, Jan. 21, 2014, Office Action.
U.S. Appl. No. 13/030,922, Jan. 8, 2014, Notice of Allowance.
U.S. Appl. No. 13/112,618, Nov. 20, 2013, Office Action.
U.S. Appl. No. 13/112,631, Dec. 2, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/791,829, Oct. 8, 2013, Notice of Allowance.
U.S. Appl. No. 13/898,202, Jan. 3, 2014, Office Action.
U.S. Appl. No. 12/684,569, Apr. 23, 2014, Office Action.
U.S. Appl. No. 12/950,628, Apr. 25, 2014, Notice of Allowance.
U.S. Appl. No. 12/961,331, Apr. 25, 2014, Notice of Allowance.
U.S. Appl. No. 13/030,922, Apr. 30, 2014, Issue Notification.
U.S. Appl. No. 11/411,925, Jun. 4, 2014, Issue Notification.
U.S. Appl. No. 11/852,190, Jun. 4, 2014, Issue Notification.
U.S. Appl. No. 12/122,603, Apr. 30, 2014, Office Action.
U.S. Appl. No. 12/848,642, Jun. 4, 2014, Issue Notification.
U.S. Appl. No. 12/941,809, Jun. 4, 2014, Issue Notification.
U.S. Appl. No. 12/987,792, Jun. 11, 2014, Office Action.
U.S. Appl. No. 11/113,549, Jul. 2, 2014, Issue Notification.
U.S. Appl. No. 11/455,993, Aug. 11, 2014, Notice of Allowance.
U.S. Appl. No. 11/674,930, Jul. 30, 2014, Issue Notification.

(56) References Cited

OTHER PUBLICATIONS

U.S. Appl. No. 12/113,851, Aug. 21, 2014, Office Action.
U.S. Appl. No. 12/393,877, Aug. 4, 2014, Notice of Allowance.
U.S. Appl. No. 12/403,277, Aug. 15, 2014, Office Action.
U.S. Appl. No. 12/950,628, Aug. 13, 2014, Issue Notification.
U.S. Appl. No. 12/961,331, Aug. 13, 2014, Issue Notification.
U.S. Appl. No. 13/898,202, Aug. 21, 2014, Office Action.

* cited by examiner

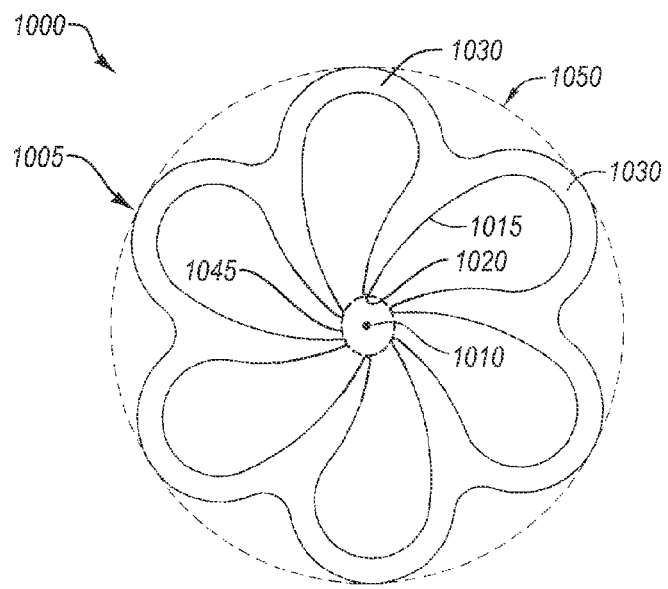
Fig. 10
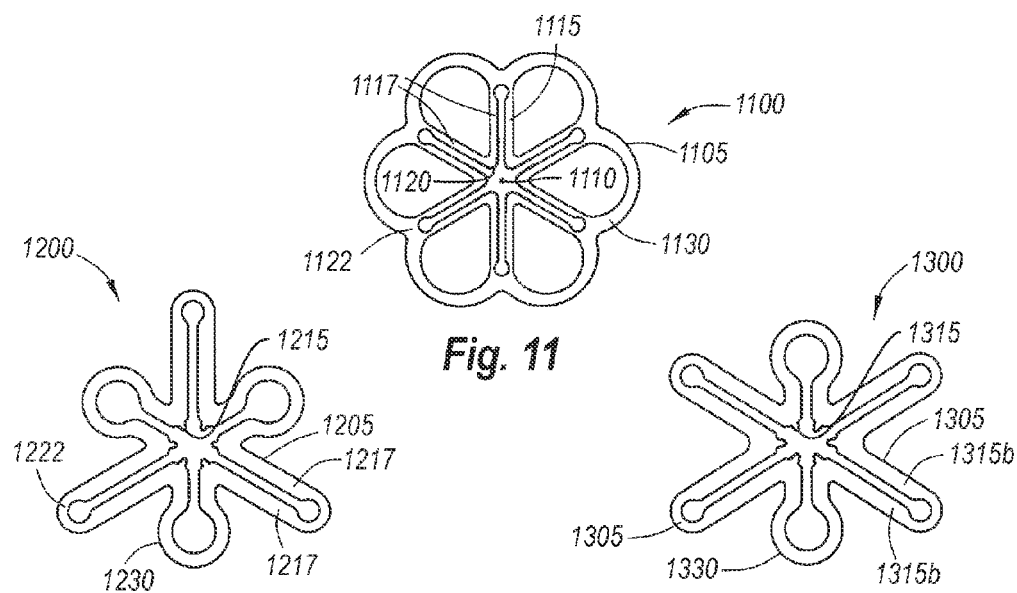
Fig. 11
Fig. 12
Fig. 13

CURVED CLOSURE DEVICE

CROSS-REFERENCE TO RELATED APPLICATION

This application claims the benefit of and priority to U.S. Provisional Patent Application Ser. No. 61/141,597, filed Dec. 30, 2008, and entitled "Curved Closure Device", the entirety of which is hereby incorporated by reference. This application also claims the benefit of and priority to U.S. Provisional Patent Application Ser. No. 61/139,995, filed Dec. 22, 2008, and entitled "Closure Device", the entirety of which is hereby incorporated by reference. This application also claims the benefit of and priority to U.S. patent application Ser. No. 12/481,377, filed Jun. 9, 2009, and entitled "Closure Device", which claims the benefit of and priority to U.S. Provisional Patent Application Ser. No. 61/139,995, filed Dec. 22, 2008, and entitled "Closure Device", the entireties of each are hereby incorporated by reference.

FIELD OF THE INVENTION

The present invention relates generally to medical devices, and more particular to device, apparatus, and methods for managing access through tissue.

BACKGROUND OF THE INVENTION

Catheterization and interventional procedures, such as angioplasty or stenting, generally are performed by inserting a hollow needle through a patient's skin and tissue into the vascular system. A guide wire can be advanced through the needle and into the patients blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath would be removed, leaving a puncture site in the vessel wall. Traditionally, external pressure would be applied to the puncture site until clotting and wound sealing occur; however, the patient must remain bedridden for a substantial period of time after clotting to ensure closure of the wound. This procedure, however, can be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatuses have been suggested for percutaneously sealing a vascular puncture by occluding the puncture site. For example, U.S. Pat. Nos. 5,192,302 and 5,222,974, issued to Kensey et al., describe the use of a biodegradable plug that can be delivered through an introducer sheath into a puncture site. Another technique has been suggested that involves percutaneously suturing the puncture site, such as that disclosed in U.S. Pat. No. 5,304,204, issued to Hathaway et al. Such apparatuses are often permanently deployed without regard to subsequent removal.

BRIEF SUMMARY

A closure device includes a body configured to move between a pre-deployed configuration and a deployed configuration, and a plurality of tissue-engaging portions extending from the body. At least two of the tissue-engaging portions are separated by a first distance in the deployed configuration and a second distance in the pre-deployed configuration, wherein the first distance is smaller than the second distance. In at least the deployed configuration, the body forms an inner periphery and an outer periphery such that at least a portion of the inner periphery defines a first plane. At least a portion of the body extends away the first plane between the inner periphery and the outer periphery.

In another example, the closure device includes a body being configured to move relative to a central axis between a pre-deployed configuration and a deployed configuration, wherein a first transverse axis is disposed orthogonally to the central axis and a second transverse axis is disposed orthogonally to the central axis and the first transverse axis. The closure device also includes a plurality of tissue-engaging portions extending from the body in which at least two of the tissue-engaging portions are separated by a first distance in the deployed configuration and a second distance in the pre-deployed configuration. The first distance is smaller than the second distance. The body is curved relative to at least one of the first transverse axis and the second transverse axis while in at least one of the pre-deployed configuration and the deployed configuration.

A method is also provided that includes placing a closure device into proximity with a tissue surface having a puncture defined therein in a pre-deployed configuration and moving the closure device to a deployed configuration, wherein the closure device includes a curved interior surface in contact with the tissue surface.

It is to be understood that both the foregoing general description and the following detailed description are exemplary and are intended to provide further explanation of the invention claimed.

BRIEF DESCRIPTION OF THE DRAWINGS

In order to describe the manner in which the above-recited and other advantages and features of the invention can be obtained, a more particular description of the invention briefly described above will be rendered by reference to specific examples thereof which are illustrated in the appended drawings. Understanding that these drawings depict only typical examples of the invention and are not therefore to be considered to be limiting of its scope, the invention will be described and explained with additional specificity and detail through the use of the accompanying drawings.

FIG. 10 illustrates a further example of a closure device according to one embodiment.

FIG. 11 illustrates a still further example of a closure device according to one embodiment.

FIG. 12 illustrates an example of a closure device through tissue according to one embodiment.

FIG. 13 illustrates another example of a closure device according to one embodiment.

Figure 1A:
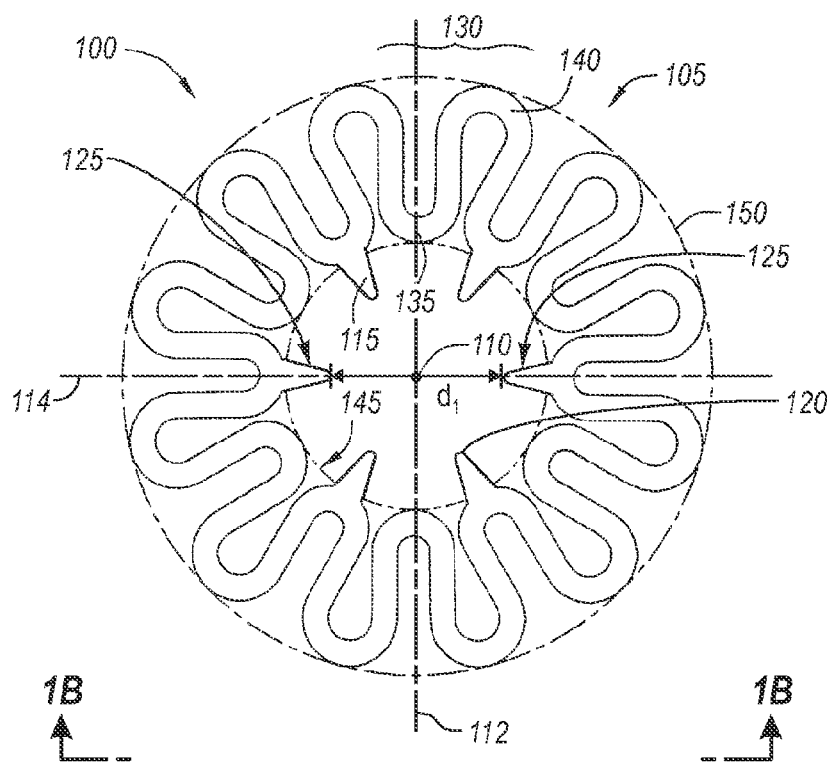
FIG. 1A is a top view of an example closure device in a deployed configuration.

It should be noted that the figures are not drawn to scale and that elements of similar structures or functions are generally represented by like reference numerals for illustrative purposes throughout the figures. It also should be noted that the figures are only intended to facilitate the description of examples of the present invention.

DETAILED DESCRIPTION

A closure device is provided herein that is curved in such a manner as to facilitate increased engagement between the closure device and the wall of the body lumen that the closure device engages. For example, the curvature of the closure device can be similar to the curvature of the wall of a body lumen.

In particular, turning now to the drawings, FIGS. 1A-1F show a first example of a closure device 100 for managing access through tissue. The closure device 100 can be used for closing an incision, puncture, or other passage through tissue. In some examples, the closure device 100 may close communication with a blood vessel or other body lumen (not shown) and of relatively large blood vessels or other body lumens in particular. The closure device 100 includes a body 105. In the present example, the body 105 can be generally annular in shape and/or may surround a central device axis 110. As used herein, an "annular-shaped body" may include any hollow body, e.g., including one or more structures surrounding an opening. Thus, although an annular-shaped body can be circular, it may include other noncircular shapes as well, such as elliptical or other shapes that are asymmetrical about a central device axis. In other examples, the body 105 may include other shapes and/or may not have a central device axis 110.

For ease of reference, a first transverse axis 112 and a second transverse axis 114 will be discussed in describing the closure device 100. In at least one example, the first transverse axis 112 can be generally perpendicular to the central device axis 110. As previously introduced, the closure device 100 may be deployed to close a puncture in tissue having curvature, such as a major body lumen. Body lumens have curved walls that may define a generally circular cross section about a central lumen axis. Returning to the closure device 100, the first transverse axis 112 may be generally parallel to the central lumen axis when deployed. Further, the closure device 100 may be curved to facilitate engagement of the closure device 100 with the curvature of the tissue. The first transverse axis and the second transverse axis will be referenced below to describe various closure devices with curvatures that may be described with reference to one or more of the first or second transverse axes 112, 114 and/or other reference points. For ease of reference, such curvature will be referred to as transverse curvature to distinguish the curvature from that applied to expandable elements 130 relative to central device axis 110 described below. Accordingly, curvature may be applied to the expandable elements 130 relative to the central device axis 110 as well as to one or more of the first and second transverse axes 112, 114 resulting in three-dimensional curvature in at least one of the expandable elements 130.

The closure device 100 for managing access through tissue may include a plurality of tissue-engaging portions 115 extending from the body 105. The tissue-engaging portions 115 may include edges 125 and/or tip portions 120. Portions of the tissue-engaging portions 115 may include tip portions 120 that are sharp and/or obtuse. Portions of the tissue-engaging portion 115 also include edges 125. In some examples, the tissue-engaging portions 115 may not have edges such that they are generally rounded.

In the present example, the tip portions 120 can be obtuse to facilitate engagement with the tissue. In some examples where the tip portion 120 is obtuse, the tip portion 120 may not substantially penetrate the tissue, but rather may engage the tissue to manage access through the tissue. For example, if the closure device 100 for managing access through tissue were used with an opening in a body lumen, the tip portions 120 may not penetrate through the tissue into the body lumen, but rather may engage the tissue near the opening (although in some examples, the tip portions 120 may partially penetrate the tissue).

Engaging tissue may include using frictional forces and/or other forces to manipulate the tissue. For example, in an example where the tissue-engaging portions 115 have tip portions 120 that are obtuse, the tip portions 120 may engage the tissue such that, as the closure device 100 moves back toward the deployed configuration, the tissue is pulled closed. In other examples, the tip portions 120 may substantially penetrate the tissue. In further examples, the tip portions 120 of primary tissue-engaging portions (not shown) may substantially penetrate the tissue while the tip portions 120 of secondary tissue-engaging portions (not shown) may not substantially penetrate the tissue. Other configurations of the tissue-engaging portions 115 and their tip portions 120 can be used.

In the present example, the body 105 may include a plurality of expandable elements 130 that can be connected to one another to form body 105. Each expandable element 130 may include an inner or first curved region 135 and an outer or second curved region 140. The first and second curved regions 135, 140 can be out of phase with one another and/or can be connected alternately to one another, thereby defining an endless sinusoidal pattern. Alternatively, other generally zigzag patterns can be provided that repeat periodically, (e.g., saw tooth or square tooth patterns), instead of the illustrated sinusoidal pattern, thereby defining inner and outer regions that may alternate about the body 105.

The plurality of tissue-engaging portions 115 can be biased to extend towards one another. In the present example, the tissue-engaging portions 115 can be biased generally inwardly into the space bounded by the inner periphery 145. In other configurations, the tissue-engaging portions 115 can be biased toward the central device axis 110. In other examples, at least two of the tissue-engaging portions 115 can be biased to extend towards each other.

In the present example, the tissue-engaging portions 115 can be disposed on the first curved regions 135 and/or oriented toward the central device axis 110 when the closure device 100 is in the deployed configuration. The tissue-engaging portions 115 can be provided in pairs opposite from one another, as in the present example. The tissue-engaging portions 115 can be provided symmetrically with respect to the central device axis 110 and/or can be provided asymmetrically.

FIG. 1A shows the closure device 100 in a deployed configuration. In the present example, when the closure device 100 is in the deployed configuration, the first curved regions 135 may define an inner periphery 145 of the body 105 and the closure device 100, and the second curved regions 140 may define an outer periphery 150. Accordingly, at least a portion of at least some of the expandable elements 130 are curved between the inner periphery 145 and the outer periphery 150.

Regardless of the configuration of the expandable elements 130, at least a portion of at least some of the expandable elements 130 are curved relative to at least one of the first and/or the transverse axes 112, 114. The first and second transverse axes 112, 114 may be co-planar with the inner periphery 145.

Figure 1B:
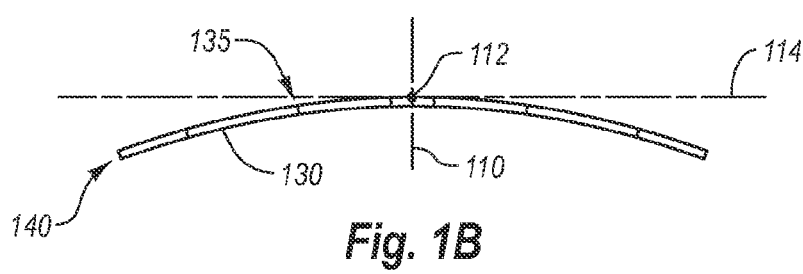
FIG. 1B is a side view of the example closure device shown in FIG. 1A in a deployed configuration.

One example of curvature in the expandable elements 130 between the inner periphery and the outer periphery is illustrated in FIG. 1B. In particular, in the view illustrated in FIG. 1B the central device axis 110 and the second transverse axis 114 are parallel to the viewing plane while the first transverse axis 112 is generally perpendicular to the viewing plane. As a result, the first transverse axis 112 extends into and out of the viewing plane.

In one example, the expandable elements 130 may be curved relative a line parallel to the first transverse axis 112. In other words, the curvature illustrated in FIG. 1B illustrates a single cross sectional view of a portion closure device 100. For ease of reference, the curvature of the closure device 100 will be described, at least initially, as being continuous along the length of the first transverse axis 112.

At least some of the expandable elements 130 extend away from a plane defined by the first and second transverse axes 112, 114 as the expandable elements 130 extend from the inner periphery 145 to the outer periphery 150. Accordingly, at least some of the outer curved regions 140 are farther away from a plane containing the first and second transverse axes 112, 114 than corresponding inner curved regions 135 are to the plane. In at least one example, the closure device 100 curves relative a single axis, such that in at least one of the pre-deployed or deployed states, at least one of an inner or outer surface defines a partially cylindrical shape. Such a configuration is illustrated in solid lines in FIG. 1E.

Figure 1C:
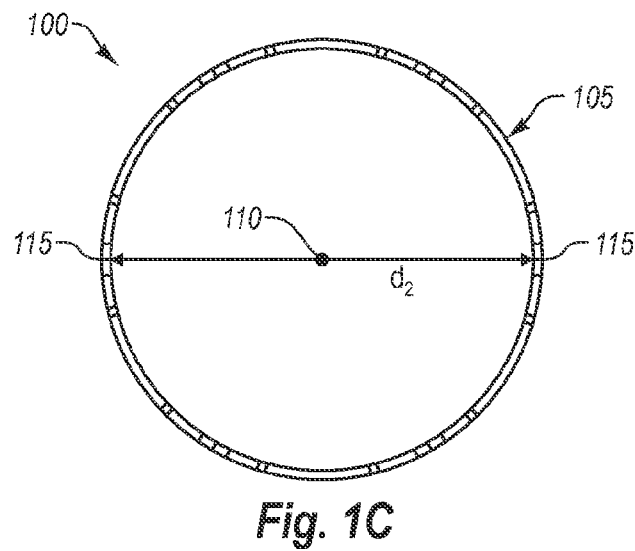
FIG. 1C is a top view of the example closure device shown in FIG. 1A in a pre-deployed configuration.
Figure 1D:
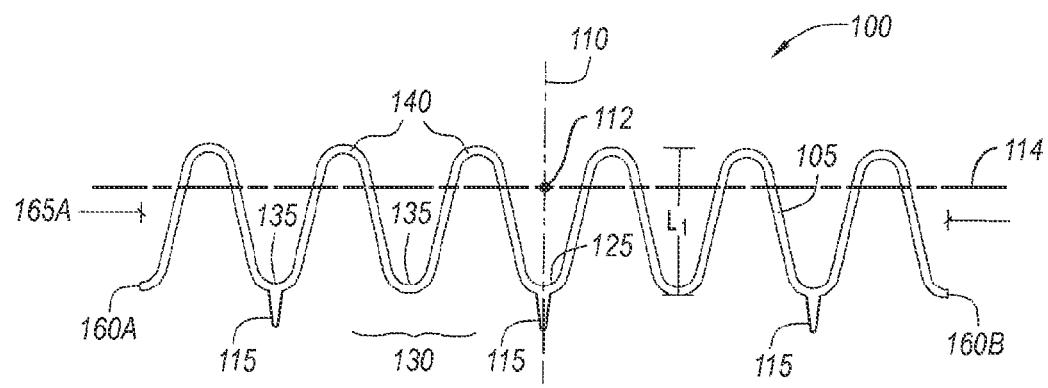
FIGS. 1D and 1E are side views of the example closure device of FIG. 1A, with the tissue-engaging portions oriented substantially transversely from a planar orientation defined by an inner periphery of the closure device, in compressed and expanded states, respectively.
Figure 1E:
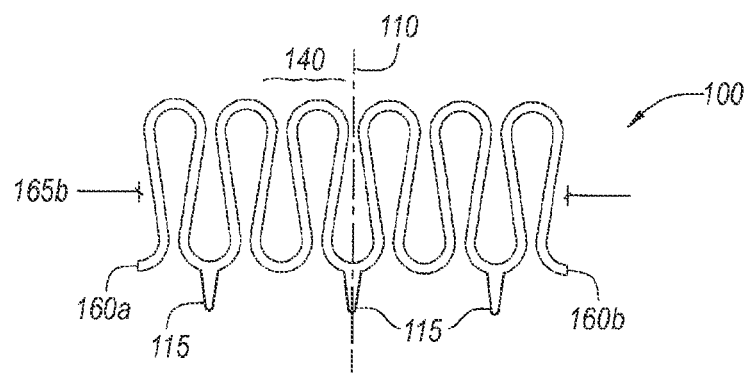
Figure 1F:
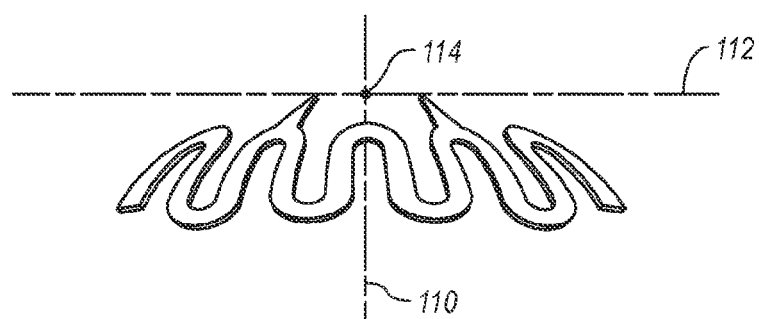
FIG. 1F is an example closure device with curvature about a first transverse axis and/or second transverse axis.

FIG. 1F illustrates a side view of a closure device 100 in which the second transverse axis 114 is generally perpendicular to the page as viewed and the first transverse axis 112 is generally parallel to the page as viewed. In other examples, the closure device 100 may curve relative to both axes such that in at least one of the pre-deployed or deployed states, at least one of an inner surface or outer surface is partially hemispherical in shape, as illustrated in dashed lines.

Returning again to FIG. 1B, a radius illustrates the curvature of the closure device. A single radius of curvature results in a circular arc that runs continuously between opposing outer curved regions 140. In other examples, the curvature of the expandable elements 130 may follow an elliptical arc. In other examples, the curvature of the expandable elements 130 may be discontinuous, such that the curved regions are separate portions with different curvature and/or no curvature. Regardless of the curvature applied to the expandable elements 130, at least a portion of the expandable elements 130 are curved to facilitate engagement between the closure device 100 and the surface of the tissue which the closure device 100 is to engage.

Additionally, as shown in FIGS. 1A-1F, the tissue-engaging portions 115 can be disposed on alternating first curved regions 135. Thus, at least one period of a zigzag pattern can be disposed between adjacent tissue-engaging portions 115, which may enhance flexibility of the closure device 100, as explained further below.

In the deployed configuration, shown in FIGS. 1A and 1B, the tissue-engaging portions 115 can be separated by a first distance, i.e. $d_1$. FIGS. 1C, 1D, and 1E illustrate the device in a pre-deployed configuration. In the pre-deployed configuration, the tissue-engaging portions 115 and the inner curved regions 135 of the body are rotated out of a plane defined by the first and second transverse axes 112, 114. As shown in FIG. 1C, the body 105 and/or the tissue-engaging portions 115 can be deflected into the pre-deployed configuration. In the present example, the tissue-engaging portions 115 may extend transversely with respect to a plane containing the first and second transverse axis 112, 114, thereby defining the pre-deployed configuration for the closure device 100.

In other examples, the body 105 and/or the tissue-engaging portions 115 in the pre-deployed configuration may not extend transversely with respect to a plane defined in the deployed configuration. For example, the body 105 and/or the tissue-engaging portions 115 in the pre-deployed configuration may remain in a plane defined by the first and second transverse axes 112, 114.

In the pre-deployed configuration, shown in FIG. 1C, the tissue-engaging portions 115 can be separated by a second distance $d_2$. In the present example, the first distance $d_1$ (FIG. 1A) and the second distance $d_2$ can be measured from the tip portions 120 of two tissue-engaging portions 115. In other examples, the first and second distances $d_1$, $d_2$ can be measured from another portion of the tissue-engaging portions 115, for example from the base (not shown) of the tissue-engaging portions 115. The first distance $d_1$, in the present example, can be smaller than the second distance $d_2$, such that the distance $d_1$ in the deployed configuration can be smaller than the distance $d_2$ in the pre-deployed configuration.

The first and second distances $d_1$, $d_2$ may vary before deployment, pre-deployment, and/or when providing access through the tissue post deployment. With continued reference to FIG. 1C, before being deployed in tissue, the closure device 100 for managing access through tissue can be substantially in the pre-deployed configuration such that two tissue-engaging portions 115 can be separated by about the second distance $d_2$. When deployed in tissue, the closure device 100 can be substantially in the deployed configuration illustrated in FIG. 1A such that the two tissue-engaging portions 115 can be separated by about the first distance $d_1$.

In the present example, the tissue-engaging portions 115 can be oriented substantially parallel to the central device axis 110 in the pre-deployed configuration, as shown in FIG. 1C. In this pre-deployed configuration, the body 105 may have a generally annular shape, which may be curved relative to one or more of the first or second axes 112, 114, as described above. The body 105 can be sufficiently flexible such that the closure device 100 may assume a generally circular or elliptical shape, e.g. substantially conforming to an exterior surface of a delivery device (not shown) used to deliver the closure device 100 for managing access through tissue.

The tissue-engaging portions 115 and/or body 105 can be biased to move from the pre-deployed configuration towards the deployed configuration of FIG. 1A. Thus, with the tissue-engaging portions 115 in the pre-deployed configuration, the tissue-engaging portions 115 may penetrate and/or be engaged with tissue at a puncture site. When the closure device 100 is released, the tissue-engaging portions 115 may attempt to return towards one another (i.e. the distance may decrease from the second distance $d_2$ toward the first distance $d_1$) as the closure device 100 moves towards the deployed configuration, thereby drawing the engaged tissue together and substantially closing and/or sealing the puncture site, as explained further below.

The expandable elements 130 may distribute stresses in the closure device 100 for managing access through tissue as the device moves between the deployed and pre-deployed configurations, thereby generally minimizing localized stresses that may otherwise plastically deform, break, and/or otherwise damage the closure device 100 during delivery. Further, the curvature applied to the expandable elements 130 as described above may enhance engagement between the closure device 100 and the tissue it engages.

In addition, when the closure device 100 is in the pre-deployed configuration, the expandable elements 130 can be movable between a compressed state, such as that shown in FIG. 1E, and an expanded state, such as that shown in FIG. 1D (where opposite ends 160a, 160b are connected to one another). The body 105 can be biased towards the expanded state, but can be compressed to the compressed state, e.g., by constraining the closure device 100. Alternatively, only a portion of the body 105 can be biased towards the expanded state. For example, in the present example, the first curved regions 135 and/or the expandable elements 130 can be biased towards the compressed state. Furthermore, the expandable elements 130 may reduce the force required to be exerted on the closure device 100 to transition the closure device 100 from the deployed configuration to the pre-deployed configuration before loading onto a delivery device (not shown).

With the closure device 100 in the pre-deployed configuration, the expandable elements 130 can be circumferentially and/or radially compressed to the compressed state until the closure device 100 defines a first diameter or circumference 165b, such as that shown in FIG. 1E. The closure device 100 can be constrained in the compressed state, e.g., by loading the closure device 100 onto a carrier assembly of a delivery device (not shown), as described further below. When released from the constraint, e.g., when deployed from the carrier assembly, the closure device 100 may automatically expand towards the expanded state, such as that shown in FIG. 1D, thereby defining a second diameter or circumference 165A. Thus, the expandable elements 130 may facilitate reducing the profile of the closure device 100 during delivery, e.g., to facilitate introducing the closure device 100 through a smaller puncture or passage. Once the closure device 100 is deployed entirely from the delivery device, the expandable elements 130 may resiliently expand as the closure device 100 returns towards the deployed configuration.

A closure device 100 can be partially coated with radiopaque material by using masking techniques. For example, the entire closure device 100 may first be coated with radiopaque material. The closure device 100 may then be masked at locations where the radiopaque coating is desired. For example, the expandable elements 130 of the closure device 100 can be left unmasked during this process if it is desired to leave selected expandable elements 130 uncoated by radiopaque material. This can be desirable, e.g., to prevent radiopaque material from adversely affecting the flexibility of the body 105. The closure device 100 may then be treated to remove the radiopaque material from the unmasked areas, in this example, the body 105. By providing radiopaque portions, the curvature of the closure device 100 may be aligned relative to the curvature of the tissue that the closure device 100 is to engage.

In some examples, the device 100 may include a bioactive agent. The bioactive agent can be associated with a base coat and/or top coat and/or incorporated or otherwise applied to a supporting structure of the closure device 100.

The bioactive agent may have any therapeutic effect. Examples of suitable therapeutic properties may include antiproliferative, anti-inflammatory, anti-tissue-engaging portionoplastic, anti-platelet, anti-coagulant, anti-fibrin, anti-thrombonic, anti-mitotic, antibiotic, anti-allergic, antioxidant properties, and/or other therapeutic properties.

For example, a bioactive agent can be used to reduce scar tissue response when the closure device 100 is deployed in tissue. Reducing scar tissue response, structural tissue response, restenosis, and/or thrombosis may facilitate access to the tissue after the closure device 100 is deployed. For example, if a device did not use a beneficial agent to reduce scar tissue response, structural tissue response, restenosis, and/or thrombosis after deployment, these and/or other tissue responses may hinder future access to the tissue.

In some examples, silver and/or alloys of silver can be incorporated into at least a portion of the closure device 100. For example, silver and/or alloys of silver can be included as a component of a mixture that can be incorporated into the material of the closure device 100. In particular, in at least one example the closure device may be initially formed from a flat sheet of material. The sheet may then be rolled on a dye or other apparatus to apply the selected curvature(s) to the flat sheet. In examples where a closure device 100 is formed from a sheet of material, the sheet of material may include silver and/or alloys of silver as a component of the material. In examples where the closure device 100 is formed from a wire as described in U.S. Pat. No. 6,719,777, the wire may include silver and/or alloys of silver as a component of the wire.

In other examples, at least a portion of the closure device 100 may include a coating that includes silver and/or alloys of silver as a component of the coating. For example, a coating of silver and/or alloys of silver can be applied to a portion of the surface of the closure device 100. Coatings can be applied using various coating methods. Coating methods may include physical vapor deposition, chemical vapor deposition, ion beam assisted deposition, electroplating and/or other coating methods. Physical vapor deposition may include sputter deposition and/or other physical vapor deposition methods.

Figure 2A:
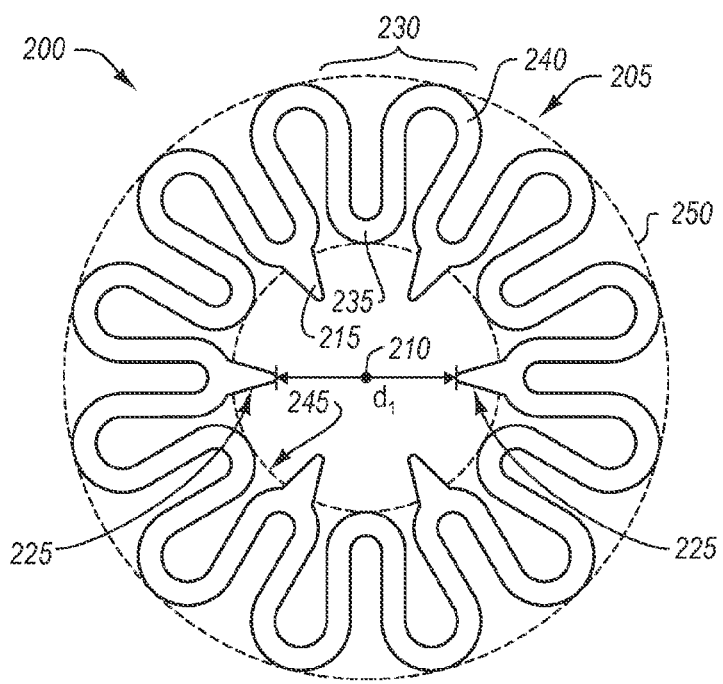
FIGS. 2A-2C are views of an example closure device according to one embodiment.
Figure 2B:
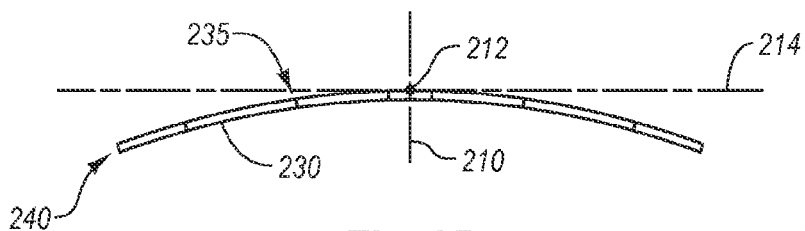
Figure 2C:
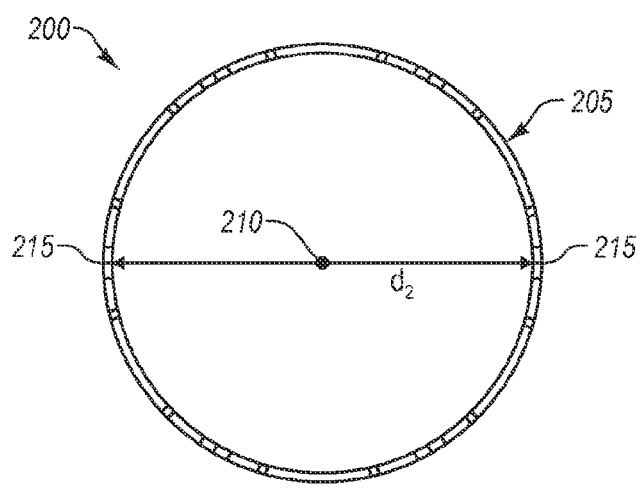

FIGS. 2A-2C illustrate a device 200 similar to the closure device 100 illustrated in FIGS. 1A-1F in which similar parts have similar numbers that are increased by 100. Accordingly, the device 200 illustrated in FIG. 2A includes a body 205 having tissue engagement portions 215 disposed on curved regions 235 of expandable elements 230. The closure device 200 is curved such that at least a portion of at least some of the expandable elements 230 are curved. As a result, as illustrated in FIG. 2A, at least a portion of the inner periphery 245 may be separated by a distance $d_1$ from the outer periphery 250. Accordingly, a portion of the inner periphery 245 and a portion of the outer periphery 250 can be offset relative to each other. The offset distance between the inner periphery 245 and the outer periphery 250 can be constant or can vary in several ways. For example, as illustrated in FIG. 2B inner periphery 245 and outer periphery 250 can be offset along the first transverse axis 212 as illustrated in solid lines or can be offset relative to both the first transverse axis 212 and the second transverse axis 214. It will be appreciated that the offsets can be uniform relative to each of the first transverse axis 212 and the second transverse axis 214 or that the offset can vary in any manner.

Figure 3A:
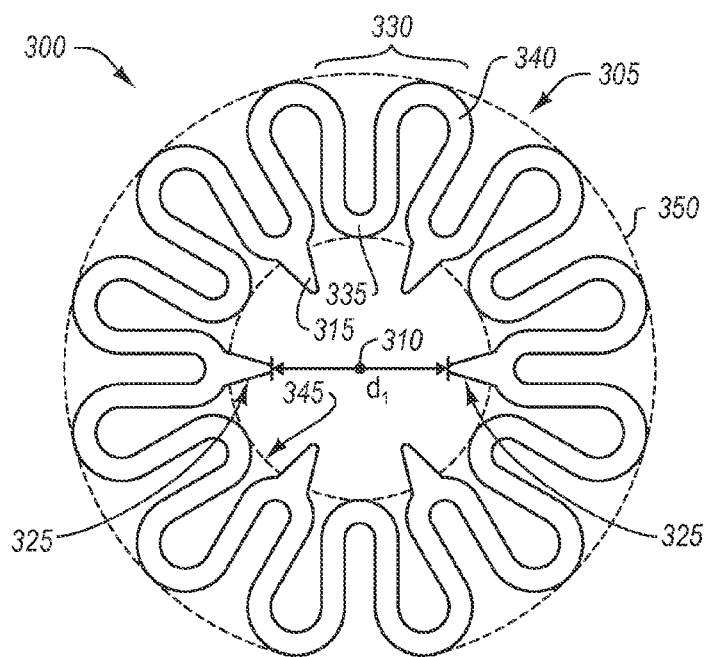
FIGS. 3A-3C are views of an additional example closure device according to one embodiment.
Figure 3B:
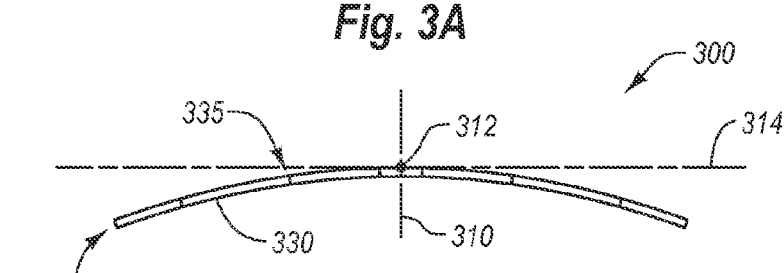
Figure 3C:
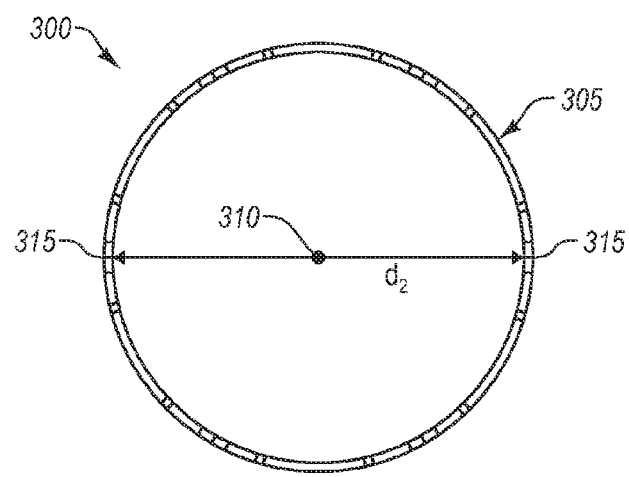

FIGS. 3A-3C illustrate an alternative example in which the closure device 300 includes one or more expandable element 330 having three-dimensional curvature applied there. For example, transverse and axial curvature may be applied the expandable elements 330 at least partially between curved regions 335 and curved regions 340 of expandable elements 330. As previously introduced, such a configuration may enhance the engagement of the closure device 300 with curved tissue surfaces.

Figure 4A:
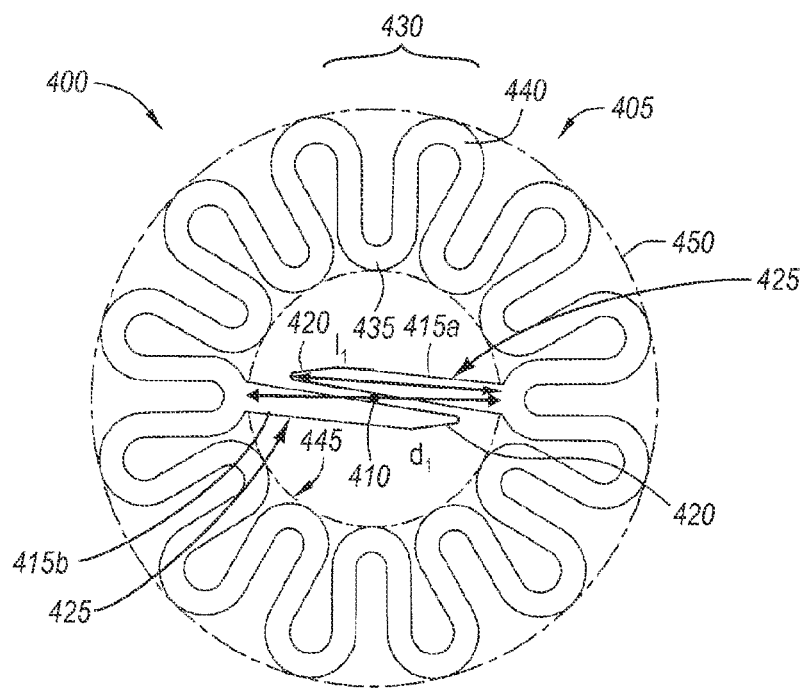
FIGS. 4A-4C illustrate another example of a closure device.
Figure 4B:
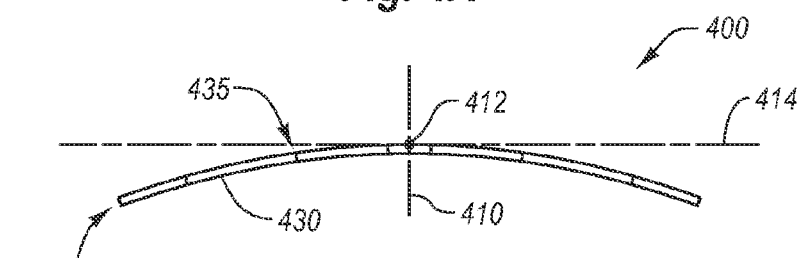
Figure 4C:
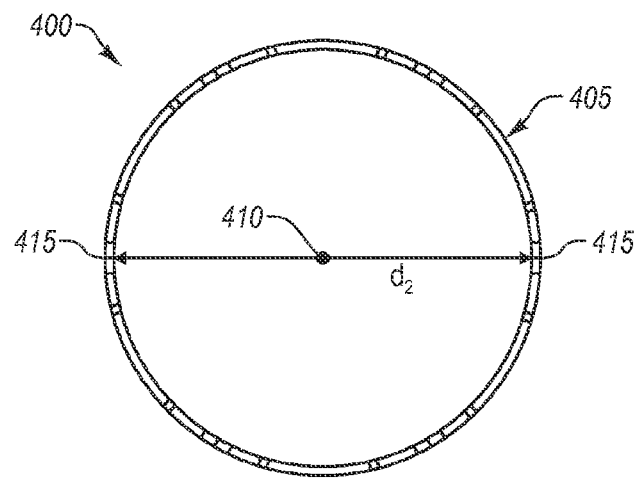

FIGS. 4A-4C illustrate another example of a closure device 400 that includes both transverse and axial curvature applied thereto. The body 405 may include a plurality of expandable elements 430 that are connected to one another to form the body 405, similar to the example of FIGS. 1A-1D. Each expandable element 430 may include an inner or first curved region 435 and an outer or second curved region 440, in a deployed configuration (shown in FIG. 4A). Similar to the example of FIGS. 1A-1D, the first and second curved regions 435, 440 may form an endless sinusoidal pattern or other generally zigzag pattern. When the closure device 400 is in the deployed configuration, the first curved regions 435 may define an inner periphery 445, and the second curved regions 440 may define an outer periphery 450.

Unlike the previous example, the closure device 400 for managing access through tissue of the present example may include only one pair of primary tissue-engaging portions 415a. The primary tissue-engaging portions 415a may have a length $l_1$, although alternatively each of the primary tissue-engaging portions 415a may have a different length than one another.

Although the length $l_1$ is illustrated as extending from a curved region 435, 440 beyond the central device axis 400, it can be possible for the length $l_1$ to be less than this distance, such as a length defined from a curved region 435, 440 to the central device axis 410 or a length defined from a curved region 435, 440 toward, but not passing the central device axis 410. The primary tissue-engaging portions 415a can be disposed in one or more opposing pairs, e.g., on opposing first curved regions 435, and can be oriented towards and/or across the central device axis 410 in the planar configuration. In the deployed configuration, the primary tissue-engaging portions 415a can be sufficiently long such that the primary tissue-engaging portions 415a at least partially overlap one another, i.e., extend across the central device axis 400 towards an opposing tissue-engaging portion 415a. Therefore, the tip portions 420 of the primary tissue-engaging portions 415a may extend past the central device axis 410 and/or the primary tissue-engaging portions 415a, b in each pair may lie substantially parallel to each other when the closure device 400 for managing access through tissue is in the deployed configuration. Each of the primary tissue-engaging portions 415a, b may include a variety of tip portions 420 and/or edges 425.

As shown in FIG. 4C, the body 405 and/or the primary tissue-engaging portions 415a, b can be deflected into the pre-deployed configuration, similar to the example of FIGS. 1A-1D. In the present example, the primary tissue-engaging portions 415a may extend transversely with respect to a plane defined by the first and second transverse axes 412, 414 in the deployed configuration, thereby defining the pre-deployed configuration for the closure device 400.

The primary tissue-engaging portions 415a, b and/or body 405 can be biased to move from the pre-deployed configuration towards the deployed configuration of FIG. 4A. Thus, with the primary tissue-engaging portions 415a, b in the pre-deployed configuration, the primary tissue-engaging portions 415a, b may penetrate and/or be engaged with tissue at a puncture site. When the closure device 400 is released, the primary tissue-engaging portions 415a may attempt to return towards one another (i.e. the distance may decrease from a second distance toward a first distance) as the closure device 400 moves towards the deployed configuration, thereby drawing the engaged tissue together and substantially closing and/or sealing the puncture site.

The primary tissue-engaging portions 415a of the present example may include the tip portions 420 and/or edges 425. For example, the tip portions 420 and/or the edges 425 of the primary tissue-engaging portions 415a, in the present example, can be obtuse.

FIGS. 5A-5E illustrate a further example of a closure device 500 for managing access through tissue according the present invention. In the present example, the device 500 may include a body 505 that includes both axial curvature as well as transverse curvature applied to a plurality of expandable elements 530. The body may include expandable elements 500 and tissue-engaging portions 515, similar to the previous examples. The reference numbers for elements of the device 500 are consistent with like elements used for the devices 100, 200, 300, 400.

The device 500 for managing access through tissue of the present example may include a plurality of primary tissue-engaging portions 515a and a plurality of secondary tissue-engaging portions 515b. Each of the primary and secondary tissue-engaging portions 515a, 515b may include a variety of tip portions 520 and/or edges 525.

The primary tissue-engaging portions 515a can be similar to the primary tissue-engaging portions 515a of the previous example. However, each of the secondary tissue-engaging portions 515b can be disposed on a first or inner curved region 535, e.g., such that one or more secondary tissue-engaging portions 515b can be provided between opposing pairs of primary tissue-engaging portions 515a. Each of the secondary tissue-engaging portions 515b may have a length $l_2$ that is substantially less than the length, $l_1$, of the primary tissue-engaging portions 515a.

Although the length $l_1$ is illustrated as extending from a curved region 535, 540 beyond the central device axis 510, it can be possible for the length $l_1$ to be less than this distance, such as a length defined from a curved region 535, 540 to the central device axis 510 or a length defined from a curved region 535, 540 toward, but not passing the central device axis 510. A secondary tissue-engaging portion 515b can be disposed on either side of each primary tissue-engaging portion 515a, in the present example. For example, the device 500 for managing access through tissue may include first and second primary tissue-engaging portions 515a. Each of the first and second primary tissue-engaging portions 515a may include a secondary tissue-engaging portion 515b on either side of it. Thus, the device 500 may include a total of two primary tissue-engaging portions 515a and four secondary tissue-engaging portions 515b. The secondary tissue-engaging portions 515b, in the present example, can be disposed substantially symmetrically about the central device axis 510. The tissue-engaging portions 515a, 515b can be provided on every other first curved regions 535. For example, a first curved region 535 having neither a primary tissue-engaging portion 515a nor a secondary tissue-engaging portion 515b may separate each adjacent tissue-engaging portion, e.g., between two adjacent secondary tissue-engaging portions 515b, or between a secondary tissue-engaging portion 515b and a primary tissue-engaging portion 515a. The primary and secondary tissue-engaging portions 515a, 515b may also include other orientations and arrangements.

Figure 5A:
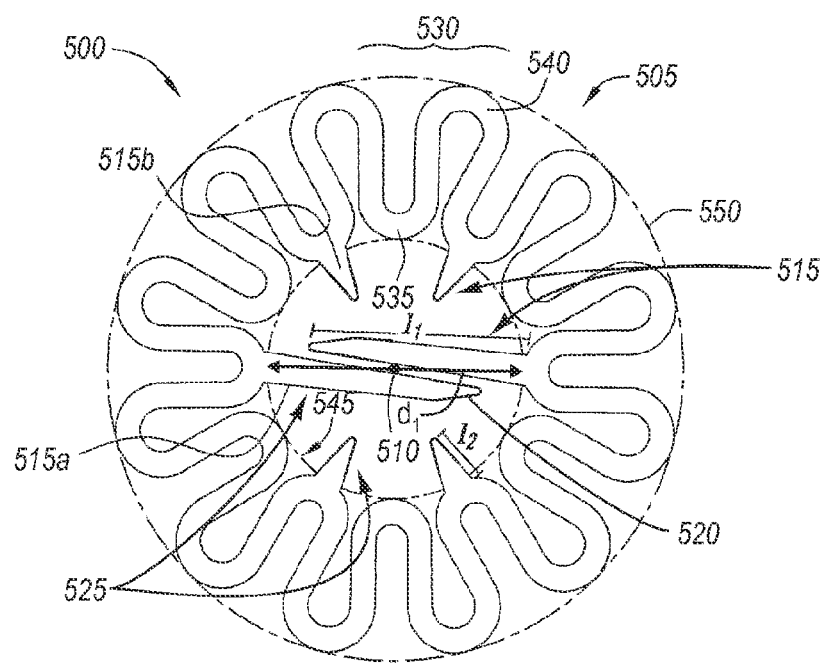
FIGS. 5A-5E illustrate further examples of a closure device.
Figure 5B:
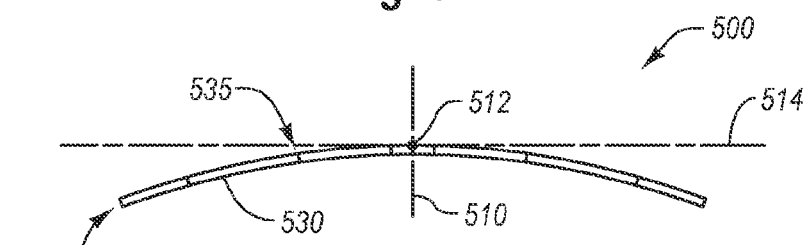
Figure 5C:
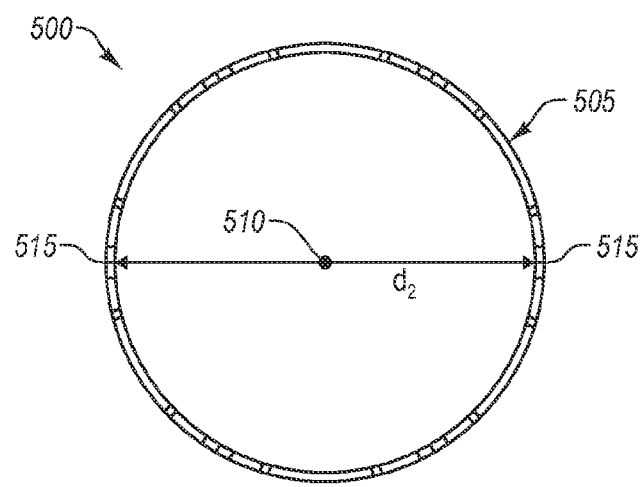
Figure 5D:
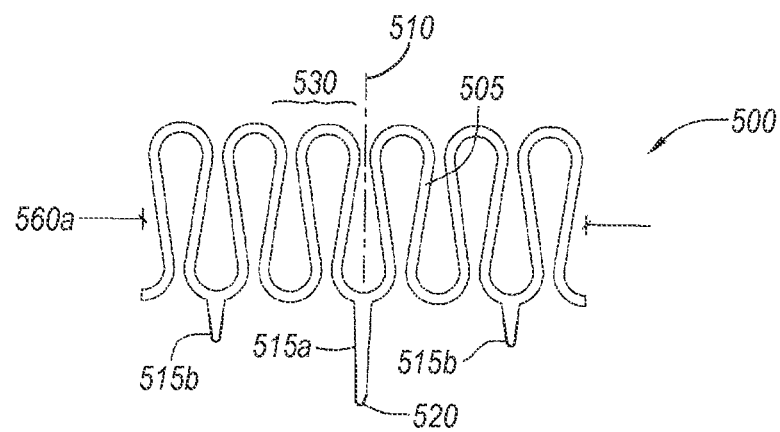
Figure 5E:
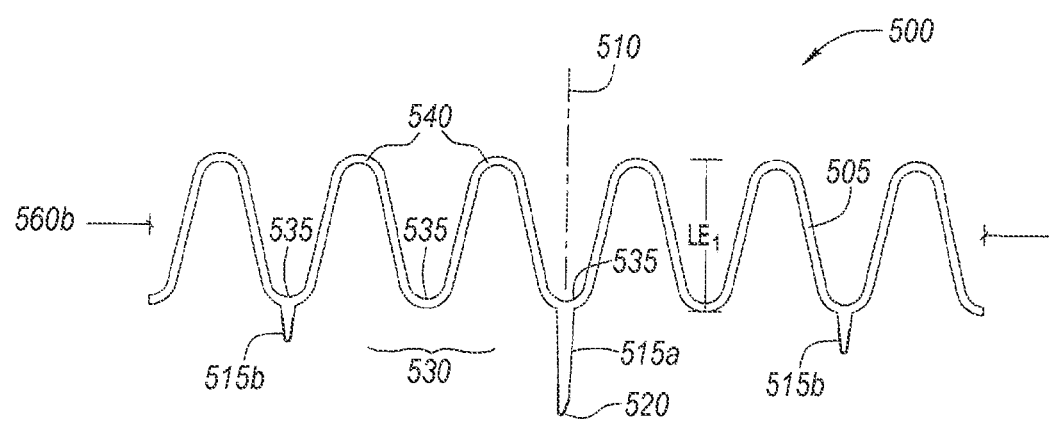

The device 500 can be moved from the deployed configuration of FIG. 5A to the pre-deployed configuration, as shown in FIGS. 5C-5E. In the present example, the body 505 and/or the tissue-engaging portions 515a, 515b can be deflected into the pre-deployed configuration such that they extend transversely with respect to the plane defined in FIG. 5A. The primary tissue-engaging portions 515a and/or secondary tissue-engaging portions 515b can be oriented substantially parallel to the central device axis 510 in the pre-deployed configuration, as shown in FIGS. 5C-5E. In the pre-deployed configuration of the present example, the body 505 may have a generally annular shape defining a length (not shown), which extends generally parallel to the central device axis 510, and corresponds generally to an amplitude of the sinusoidal pattern. The body 505 can be sufficiently flexible such that the device 500 may assume a generally circular or elliptical shape, as shown in FIG. 5C, e.g., conforming to an exterior surface of a delivery device (not shown).

The tissue-engaging portions 515a, 515b can be biased towards one another and/or towards the central device axis 510, i.e., due to the bias of the device 500 towards the deployed configuration of FIG. 5A. With the device 500 in the pre-deployed configuration, the device 500 can be delivered such that the primary tissue-engaging portions 515a, in the present example, may entirely penetrate the wall of a blood vessel or other body lumen, while the secondary tissue-engaging portions 515b may only partially penetrate and/or engage the wall due to their relative lengths. In other examples, the primary tissue-engaging portions 515a may partially penetrate the wall of a blood vessel or other body lumen, while the secondary tissue-engaging portions 515b may partially penetrate and/or engage the wall due to their relative lengths. In further examples, the primary tissue-engaging portions 515a may engage the wall of a blood vessel or other body lumen, while the secondary tissue-engaging portions 515b may penetrate and/or engage the wall due to their relative lengths.

In the deployed configuration, shown in FIG. 5A, the primary tissue-engaging portions 515a can be separated by a first distance, i.e. $d_1$. In a pre-deployed configuration, shown in FIG. 5C, the primary tissue-engaging portions 515a can be separated by a second distance, i.e. $d_2$. In the present example, the first and second distances $d_1$, $d_2$ can be measured from the base (not shown) of the two primary tissue-engaging portions 515a. In other examples, the first and second distances $d_1$, $d_2$ can be measured from another portion of the primary tissue-engaging portions 515a, for example from the tip portions 520 of the primary tissue-engaging portions 515a. The first distance $d_1$, in the present example, can be smaller than the second distance $d_2$, such that the distance $d_1$ in the deployed configuration can be smaller than the distance $d_2$ in the pre-deployed configuration.

The distances $d_1$, $d_2$ may vary before deployment, pre-deployment, and/or when providing access through the tissue post deployment. In the present example, before being deployed in tissue, the device 500 for managing access through tissue can be substantially in the pre-deployed configuration such that the two primary tissue-engaging portions 515a can be separated by about the second distance $d_2$. When deployed in tissue, the device 500 can be substantially in the deployed configuration such that the two primary tissue-engaging portions 515a can be separated by about the first distance $d_1$. When providing access to the tissue after being deployed in tissue, the device 500 can be moved from the substantially deployed configuration substantially toward and/or to the pre-deployed configuration.

The expandable elements 500 can be expanded between a compressed state, as shown in FIG. 5D, and an expanded state, as shown in FIG. 5E, similar to the example of FIGS. 1D and 1E. The expandable elements 500 can be biased to the expanded state, but can be resiliently compressed to the compressed state, e.g., by constraining the device 500.

As described in connection with FIG. 5A, each of the secondary tissue-engaging portions 515b may have a length $l_2$ that is substantially less than the length, $l_1$, of the primary tissue-engaging portions 515a. Although the length $l_1$ in FIG. 5A is illustrated as extending from a curved region 535, 540 beyond the central device axis 510, it can be possible for the length, $l_1$, to be less than this distance, such as a length defined from a curved region 535, 540 to the central device axis 510 or a length defined from a curved region 535, 540 toward, but not passing the central device axis 510.

Figure 6A:
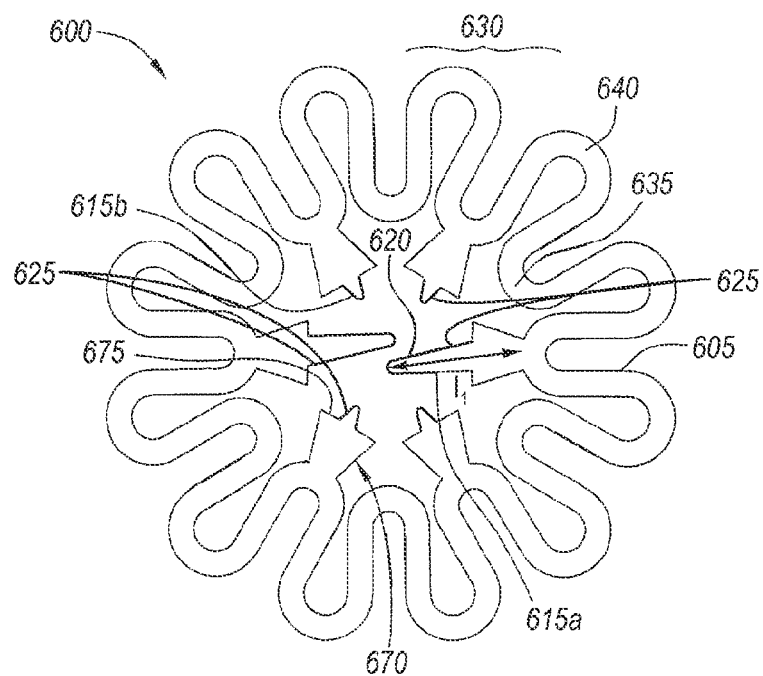
FIGS. 6A-6C illustrate another example of a closure device.
Figure 6B:
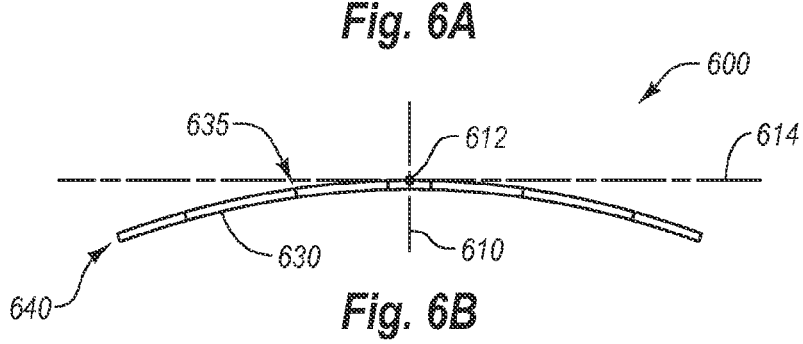
Figure 6C:
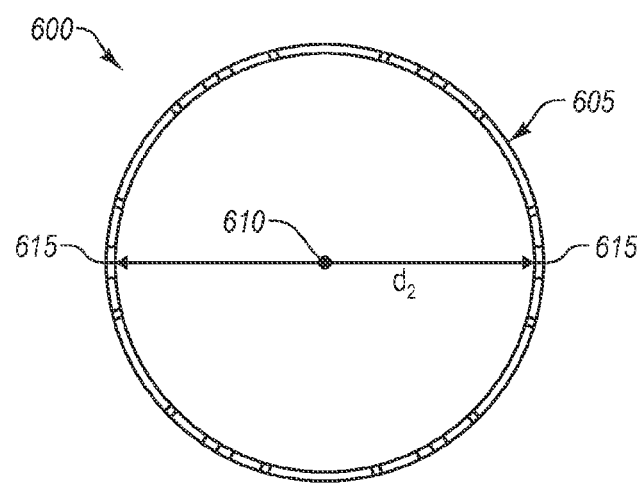

Turning to FIGS. 6A and 6B, another example of a device 600 is shown that, similar to the devices described above that may include a plurality of expandable elements 630 that interconnect to form a body 605. For example, each expandable element 630 may have a first or inner curved region 635 and a second or outer curved region 640. Several of the expandable elements 630 include both axial and transverse curvature applied thereto. Primary tissue-engaging portions 615a can be disposed on opposing first curved regions 635. Secondary tissue-engaging portions 615b can be provided on first curved regions 635 on either side of each primary tissue-engaging portion 615a. In addition, a first curved region 635 without a tissue-engaging portion 615a, 615b may separate adjacent tissue-engaging portions. Although the length $l_1$ is illustrated as extending from a curved region 635, 640 beyond the central device axis 610, it can be possible for the length $l_1$ to be less than this distance, such as a length defined from a curved region 635, 640 to the central device axis 610 or a length defined from a curved region 635, 640 toward, but not passing the central device axis 610.

The device 610 may also include stop members 660 on one or more of the tissue-engaging portions 615a, 615b, e.g., adjacent the respective first curved region 635. Each stop member 660 can be blunt-shaped. For example, the stop members 660 can be shaped generally triangularly with the blunt base 665 of the stop member 660 extending from the first curved region 635, and the tissue-engaging portion 615a, 615b extending from a wide or blunt base 665 of the stop member 660. During use, the blunt bases 665 may limit penetration of the respective tissue-engaging portions 615a, 615b into tissue by reducing an effective length of the respective tissue-engaging portion 615a, 615b. For example, when the tissue-engaging portions 615a, 615b are driven into tissue, the tissue-engaging portions 615a, 615b may penetrate the tissue until the blunt bases 665 contact the tissue, whereupon the tissue-engaging portions 615a, 615b can be prevented from penetrating further into the tissue. Stop members 660 can be used in other examples to decrease the amount of the tissue-engaging portion 615a, 615b that penetrates and/or engages surrounding tissue. Each of the tissue-engaging portions 615a, 615b may include a variety of tip portions 620 and/or edges 625.

FIGS. 7-15 show additional tissue engaging configurations in which similar numbers have been illustrated to show similar parts. Regardless of the configuration, each closure device includes expandable elements that have curvature to one or more dimension that is transverse to a central device axis.

Figure 7:
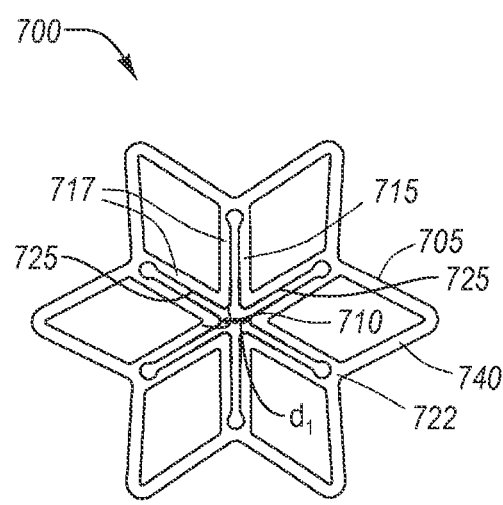
FIG. 7 illustrates a further example of a closure device.

FIG. 7 shows a further example of a closure device 700. The device 700 may include a peripheral body 705 and a plurality of tissue-engaging portions 715. Each tissue-engaging portion 715 may include a pair of legs 717 terminating in a tip portion 720. In the present example, the tissue-engaging portions 715 may be configured for penetrating and/or otherwise engaging tissue. Each of the tissue-engaging portions 715 may include a variety of tip portions 720 and/or edges 725. The tissue-engaging portions 715 may be disposed substantially symmetrically about a central axis 710. The body 705 may include a plurality of expandable elements 740 that may be connected by hinged regions 722. The hinged regions 722 may also connect adjacent tissue-engaging portions 715.

FIG. 7 shows the device 700 in a deployed configuration. In the deployed configuration, shown in FIG. 7, the tissue-engaging portions 715 may be separated by a first distance, i.e., $d_1$. Although the lengths, $l_1$, are illustrated in FIG. 7 as extending from a curved region (not shown), beyond the central axis (not shown), it may be possible for the length, $l_1$, to be less than this distance, such as a length defined from a curved region to the central axis or a length defined from a curved region toward, but not passing, the central axis.

Figure 8:
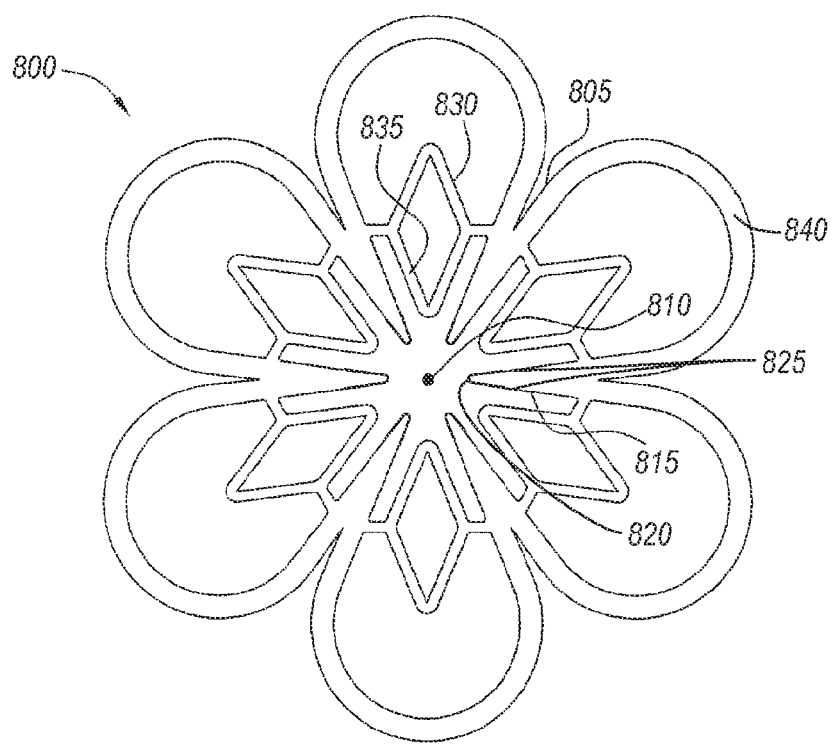
FIG. 8 illustrates an example of a closure device according to one embodiment.

Turning to FIG. 8, another example of a closure device 800 for managing access through tissue according to the present invention is shown. The closure device 800 may include a body 805, a plurality of tissue-engaging portions 815, and/or a plurality of expandable elements 830 that may interconnect adjacent tissue-engaging portions 815. The body 805 may include outer curved regions 840 that may extend between adjacent tissue-engaging portions 815, thereby defining an outer periphery (not shown) for the closure device 800. The expandable elements 830, in the present example, may be spring elements.

The closure device 800 may be moveable between a deployed configuration, such as that shown in FIG. 8, and a pre-deployed configuration, which is substantially transverse to the deployed configuration in the present example. The closure device 800 may be biased towards the deployed configuration.

In the present example, the expandable elements 830 may generally be hollow diamond shaped elements, including curved inner regions 835 oriented towards the central axis 810 of the body 805 when the closure device 800 is in the deployed configuration. The expandable elements 830 may serve multiple purposes. One purpose may include biasing the closure device 800, e.g., allowing the closure device 800 to at least partially expand resiliently. For example, when the closure device 800 is deflected into the pre-deployed configuration (not shown), the expandable elements 830 may allow the tissue-engaging portions 815 to be moved away from the central axis 810 and/or one another. Thus, during deployment, the tissue-engaging portions 815 may be deflected radially outwardly or otherwise expanded to engage a larger area of tissue.

As the tissue-engaging portions 815 are expanded, the expandable elements 830 may deform to become wider (along a dimension extending generally between the adjacent tissue-engaging portions 815) and shorter (along a dimension extending generally parallel to the tissue-engaging portions 815). Once a force causing the tissue-engaging portions 815 to expand is removed, the expandable elements 830 may resiliently try to return towards their original shape, thereby pulling the tissue-engaging portions 815 substantially closer towards one another towards the deployed configuration.

Finally, after the closure device 800 is deployed, e.g., the tissue-engaging portions 815 have penetrated and/or engaged the tissue, the curved inner regions 835 may return towards the deployed configuration, and may pinch or otherwise engage tissue between the inner curved regions 835 and the adjacent tissue-engaging portions 815. Thus, contracting the expandable elements 830 may enhance the ability of the closure device 800 to seal a puncture site, e.g., by pulling engaged tissue inwardly towards the central axis 810 of the closure device 800.

Figure 9:
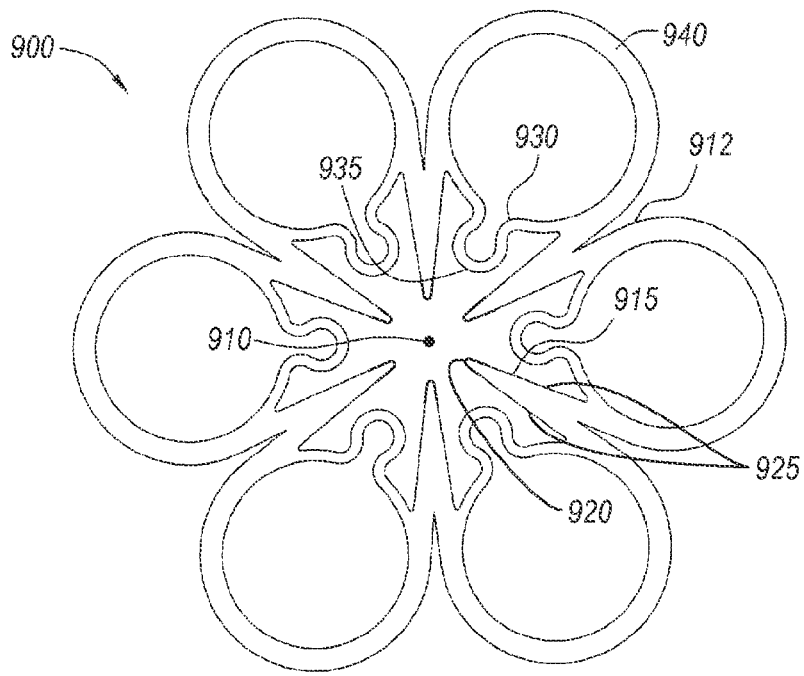
FIG. 9 illustrates another example of a closure device according to one embodiment.

FIG. 9 illustrates a further example of a closure device 900. The device 900 may be substantially similar to the device 800 shown in FIG. 8, with the exception of the shape of the expandable elements 930. In the present example, rather than diamond shaped elements 830 in FIG. 8, the expandable elements 930 may be looped elements generally defining a circular shape.

Turning now to FIG. 10, this is another example of a closure device 1000. The closure device 1000 may include a body 1005 that may be generally annular-shaped and/or may define a plane. In the present example, the body 1005 may be disposed about a central axis 1010 that may extend through the plane. The body 1005 may include a plurality of outer curved elements 1030 that may extend between adjacent tissue-engaging portions 1015 and may be connected to each other to form the body 1005. When the closure device 1000 is in the deployed configuration, the curved elements 1030 may define an outer periphery 1050 of the closure device 1000.

The tissue-engaging portions 1015 may be curved or arcuately shaped and may include tip portions 1011 that may extend toward the central axis 1010 when the closure device 1000 is in a deployed configuration. The curves of the tissue-engaging portions 1015 may all be in phase with one another such that the tissue-engaging portions 1015 spiral about the central axis 1010. This may allow a length of the tissue-engaging portions 1015 to be maximized for a given diameter of the body 1005.

For example, the tissue-engaging portions 1015 may have a length that is greater than a radius of the body 1005 without the tip portions 1011 of the tissue-engaging portions 1015 touching one another. Thus, due to the arcuate shape of each tissue-engaging portion 1015, the tissue-engaging portions 1015 of the closure device 1000 may be generally longer than the straight tissue-engaging portions of the previous devices having comparable diameters. The tissue-engaging portions 1015 may, therefore, penetrate deeper into and/or apply more pressure to tissue than the tissue-engaging portions of the other devices.

The body 1005 and/or the tissue-engaging portions 1015 of the closure device 1000 may be deflected until the tissue-engaging portions 1015 extend transversely with respect to the deployed configuration, thereby defining a pre-deployed configuration (not shown), which may be transverse in the present examples. In the pre-deployed configuration, the tissue-engaging portions 1015 may be oriented substantially parallel to the central axis 1010. Additionally, the tissue-engaging portions 1015 and/or body 1005 may be biased to move from the pre-deployed configuration towards the deployed configuration. The closure device 1000 may be delivered in substantially the same manner as will be described with respect to other devices of the present invention.

Turning to FIG. 11, this is another example of a device 1100. The device 1100 may include a peripheral body 1105 and a plurality of tissue-engaging portions 1115. Each tissue-engaging portion 1115 may include a pair of legs 1117 terminating in a tissue-engaging portion 1115. The tissue-engaging portions 1115 may be disposed substantially symmetrically about a central axis 1110. The body 1105 may include a plurality of expandable elements 1130. The expandable elements 1130 may be connected by hinged regions 1122 that may also connect adjacent tissue-engaging portions 1115.

The tissue-engaging portions 1115 may be deflected from a deployed configuration, shown in FIG. 11, to a pre-deployed configuration (not shown). In the present example, the tissue-engaging portions 1115 may be deflected such that they extend substantially transversely from the body 1105 to the pre-deployed configuration. In this pre-deployed configuration, the tissue-engaging portions 1115 may be oriented substantially parallel to the axis 1110 such that the body 1105 has a generally annular shape (not shown). The tissue-engaging portions 1115 may be biased from the pre-configured configuration towards the deployed configuration shown in FIG. 11.

The expandable elements 1130 may have a generally arcuate shape that may be expandable from a first width to a second wider width. Thus, the expandable elements 1130 may be biased to the expanded state, but may be compressed to the compressed state.

Turning to FIG. 12, this is another example of a closure device 1200. The closure device 1200 may include a peripheral body 1205 including a plurality of legs 1217 extending between tissue-engaging portions 1215, expandable elements 1230, and/or hinged regions 1222. The closure device 1200 may be formed from a single sheet of material, similar to examples described above.

The tissue-engaging portions 1215 may be biased to a deployed configuration, as shown. The body 1205 may be deflectable to a pre-deployed configuration (not shown). In the present example, the tissue-engaging portions 1205 may be oriented substantially transversely with respect to the plane of the sheet in the pre-deployed configuration. The body 1205, and particularly the legs 1217 in the present example, may be sufficiently flexible such that the closure device 1200 may assume a generally annular shape in the pre-deployed configuration, e.g., to facilitate loading of the closure device 1200 for managing access through tissue onto a delivery device (not shown).

The expandable elements 1230 may be substantially enclosed loops that may at least partially open from a compressed state (shown in FIG. 12), to an expanded state (not shown). The loops may be biased to the expanded state, similar to examples described above, thereby allowing the closure device 1200 for managing access through tissue to assume a reduced diameter and an expanded diameter.

Turning to FIG. 13, this is a further example of a closure device 1300. The closure device 1300, in the present example, may include two expandable elements 1330. The expandable elements 1330 may be disposed in a substantially symmetrical arrangement to facilitate expansion of the closure device 1300 in a generally uniform manner.

Figure 14:
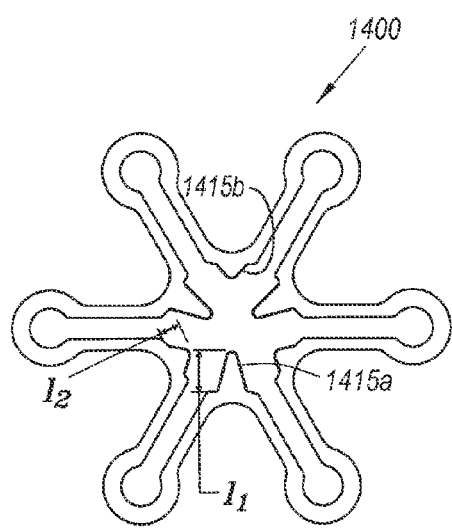
FIG. 14 illustrates a further example of a closure device according to one embodiment.

In a further example of a closure device 1400 shown in FIG. 14, the closure device 1400 may include primary tissue-engaging portions 1415a having a first length $l_1$, and secondary tissue-engaging portions 1415a having a second length $l_2$ that may be substantially shorter than the first length $l_1$. In the present example, the closure device 1400 may be deployed such that the primary tissue-engaging portions 1415a penetrate into and/or engage tissue, i.e., the wall of a blood vessel, body lumen, and/or other tissue, while the secondary tissue-engaging portions 1415b may engage extra-vascular tissue, i.e., tissue between the vessel wall and the patient's skin. Thus, the closure device 1400 may simultaneously close both the opening in the vessel wall and the passage through the intervening tissue.

Figure 15:
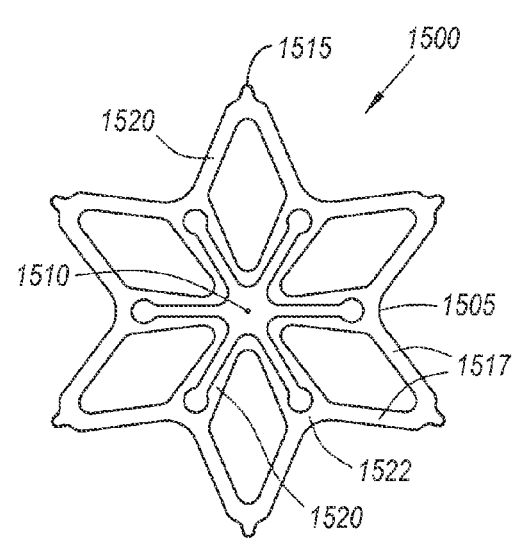
FIG. 15 illustrates a still further example of a closure device according to one embodiment.

Turning to FIG. 15, another example of a closure device 1500 for managing access through tissue is shown, in accordance with the present invention. The closure device 1500 may include a peripheral body 1505 and a plurality of tissue-engaging portions 1515 (not labeled). Each tissue-engaging portion 1515 may include a pair of legs 1517 terminating in a tip portion 1520 configured for penetrating and/or otherwise engaging tissue. The tissue-engaging portions 1515, in the present example, may be disposed substantially symmetrically about a central axis 1510. The body 1505 may include a plurality of expandable elements 1520 that are connected by hinged regions 1522 that also connect adjacent tissue-engaging portions 1515. The expandable elements 1520 may behave similar to examples described above.

In the present example, the tissue-engaging portions 1515 may be disposed radially outward in the deployed configuration. The tissue-engaging portions 1515 may be deflected such that they extend from the body 1505 in a pre-deployed configuration.

The tissue-engaging portions 1515 may be biased from the pre-deployed configuration away from one another, i.e., towards the deployed configuration. Thus, with the tissue-engaging portions 1515 in the pre-deployed configuration, the tip portions 1520 may penetrate into and/or be engaged with tissue. When the closure device 1500 for managing access through tissue is released, e.g., from within a delivery device (not shown), the tissue-engaging portions 1515 may be biased to return to the deployed configuration, thereby securing the tissue with respect to the closure device.

In addition, the closure device 1500 for managing access through tissue may include expandable elements 1520 that may be expandable from a compressed state to an expanded state, similar to some of the previous examples. The expandable elements 1520 may be biased to the expanded state, but may be compressed to the compressed state, e.g., by constraining the closure device 1500. Alternatively, any of the devices described herein may be biased to the compressed state but may be expanded to the expanded state, e.g., by constraining the closure device through tissue over a sheath or other elongated member.

Figure 16:
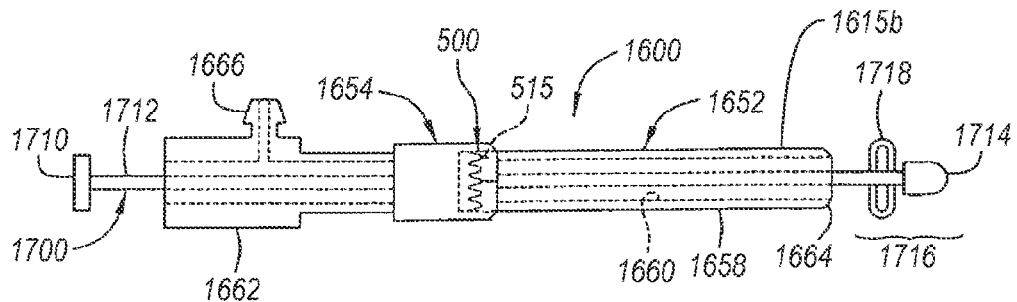
FIG. 16 illustrates an example of an apparatus suitable for delivering a closure device through tissue according to one embodiment.

The closure devices described above can be delivered using various apparatus and methods. An exemplary apparatus 1600 suitable for delivering a closure device 100 of the present invention is shown in FIG. 16. Other suitable apparatus that can be used to deliver a closure device 100 of the present invention are disclosed in co-pending U.S. patent application Ser. No. 11/427,297, entitled "Clip Applier and Methods of Use", filed Jun. 25, 2006, which is incorporated herein by reference in its entirety and which is assigned to the assignee of the present application. The disclosures of this application and any references cited therein are expressly incorporated by reference.

The apparatus 1600 may include an introducer sheath 1652 and/or a housing or carrier assembly 1654 slidably disposed on the sheath 1652. The sheath 1652 may include a substantially flexible or semi-rigid tubular body 1658 including a lumen 1660 extending between its proximal and distal ends 1662, 1664. In some examples, the distal end 1664 may have a size and/or shape configured to facilitate insertion into a blood vessel, e.g., having a tapered tip for facilitating substantially atraumatic introduction through the passage and at least partially into the vessel. In other examples, the distal end 1664 may have other sizes and/or shapes. The lumen 1660 may have a size and/or shape for inserting one or more devices therethrough. In the present example, the lumen 1660 can be configured to receive one or more medical devices, such as a catheter, guide wire, and/or other medical devices (not shown). The sheath 1652 may include one or more seals (not shown), such as a hemostatic valve, within the lumen 1660 at or near the proximal end 1662 that may provide a fluid-tight seal, while yet accommodating the insertion of one or more devices into the lumen 1660 without fluid passing proximally from the sheath 1652.

Optionally, the sheath 1652 may include a side port 1666 that may communicate with the lumen 1660, for example, to deliver fluids into the lumen 1660. Alternatively, or in addition, the side port 1666 can be used to provide a "bleed back" indicator.

The apparatus 1600 may also include a mechanical locator or obturator 1700 that can be part of an actuator assembly (not shown) that can be attachable to the proximal end of the sheath 1652. Alternatively, the mechanical locator or obturator 1700 can be a separate device that is insertable into the lumen 1660, e.g., through the actuator assembly. Generally, the obturator 1700 can be an elongate member including a distal tip 1715*a* and a distal portion 1715*b*. The distal tip 2715*a* can be substantially soft and/or flexible such that the distal tip 1715*a* may substantially atraumatically enter tissue. The distal portion 1715*b* generally includes one or more wings or other expandable elements 1718 for providing tactile feedback, as described further below.

The carrier assembly 1654 can be slidably disposed on an exterior of the sheath 1652. The carrier assembly 1654 can be configured for releasably carrying a closure device 500 for managing access through tissue (shown in phantom), which may incorporate elements of the various examples of the devices described herein. The carrier assembly 1654 can be substantially permanently attached to the sheath 1652 and/or can be actuated from the proximal end 1662 of the sheath 1652, for example, by the actuator assembly (not shown), to advance the closure device 500 distally during deployment. Alternatively, the closure device 500 can be carried by an actuator assembly.

Turning to FIGS. 17A-17F, the apparatus 1600 can be used to deliver the closure device 500 for managing access through tissue. In the present example, the closure device 500 can be used to substantially close and/or seal an incision, puncture, or other passage 1692 that extends from a patient's skin 1694, through intervening tissue 1696, and into a wall 1898 of a vessel 1890 or other body lumen. Alternatively, the apparatus 1600 can be used to deliver the closure device 500 to engage tissue in other procedures, e.g., to connect tissue segments together or otherwise to secure tissue structures with respect to one another. For example, the apparatus 1600 and closure device 500 can be used to attach an anastomosis during a bypass procedure. In another example, the apparatus 1600 and closure device 500 can be used to close an aperture (i.e. a puncture, cut, tear, and/or other aperture) on the surface of the patient's skin 1694. Although the closure device 500 and/or apparatus 1600 can be useful in a variety of procedures, the following example illustrates the usefulness of the closure device 500 and/or apparatus 1600 to substantially close and/ or seal an incision, puncture, or other passage 1692 that extends from a patient's skin 1694, through intervening tissue 1696, and into a wall 1898 of a vessel 1890 or other body lumen.

Figure 17A:
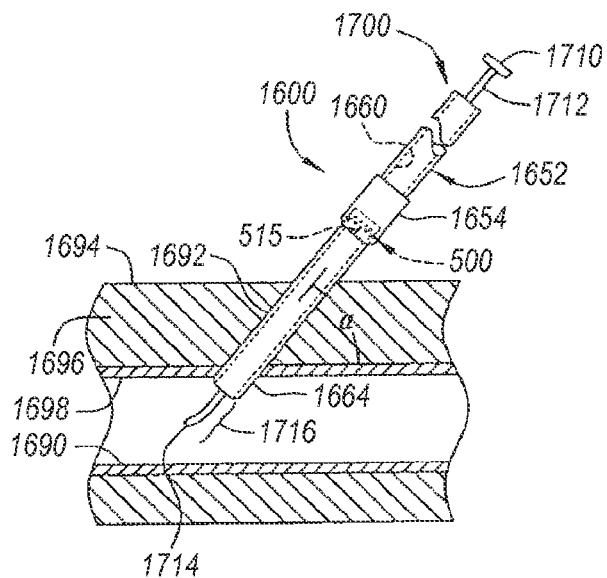
FIGS. 17A-17F are cross-sectional views of a blood vessel, showing a method for delivering a closure device through tissue into a passage communicating with the vessel using the apparatus of FIG. 16.

As shown in FIG. 17A, the sheath 1652 can be inserted or otherwise positioned within the vessel 1890, i.e., through the passage 1692. The sheath 1652 can be advanced over a guide wire or other rail (not shown) previously positioned through the passage 1692 into the vessel 1890 or advanced in conjunction with a pointed stylet directly through tissue using conventional procedures. The vessel 1890, in the present example, can be a peripheral vessel, such as a femoral, radial, or carotid artery, although other body lumens can be accessed using the sheath 1652.

The passage 1692, and consequently the sheath 1652, can be oriented at an angle "alpha" with respect to the vessel 1890, thereby facilitating introducing devices through the lumen 1660 of the sheath 1652 into the vessel 1890 with minimal risk of damage to the vessel 1890. One or more devices, such as a guide wire, a catheter, and the like (not shown), can be inserted through the sheath 1652 and advanced to a desired location within the patient's body. In the present example, the devices can be used to perform a first therapeutic or diagnostic procedure, such as angioplasty, atherectomy, stent implantation, and/or other procedure, within the patient's vasculature. In other examples, other procedures can be performed.

After the first procedure is complete, any devices used during the procedure can be removed from the sheath 1652, and the obturator 1700 can be inserted into the lumen 1660. For example, the obturator 1700 can be part of an actuator assembly (not shown), and can be advanced through the lumen when the actuator assembly is attached to the proximal end of the sheath 1652. Alternatively, the actuator assembly and obturator 1700 can be coupled separately to the sheath 1652.

When the obturator 1700 is fully inserted within the sheath 1652, the distal portion 1715*b* of the obturator 1700 may extend beyond the distal end 1664 of the sheath 1652. In an alternative example, the obturator 1700 can be attached to an exterior surface (not shown) of the sheath 1652, for example, along a track, e.g., including cooperating slots, grooves, and the like (not shown) in the sheath 1652 and obturator 1700.

Figure 17B:
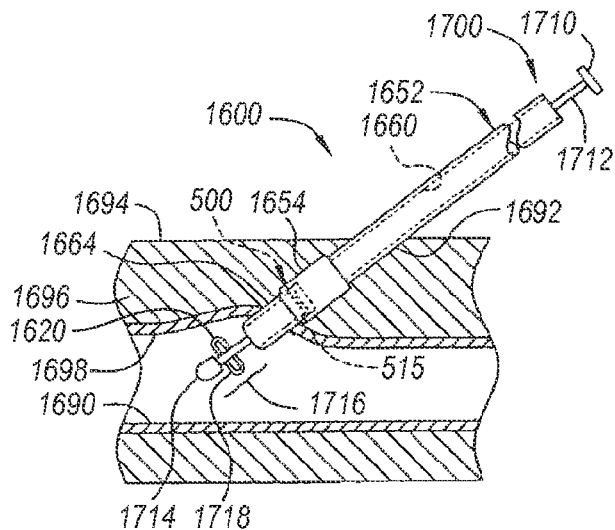

Turning to FIG. 17B, the expandable elements 1718 on the distal portion of the obturator 1700 may then be directed to their expanded configuration, for example, by activating a switch on the proximal end (not shown) of the obturator 1700. In some examples, the sheath 1652 and obturator 1700 can be coupled to one another, such that the sheath 1652 and obturator 1700 can be moved in conjunction with one another.

Figure 17C:
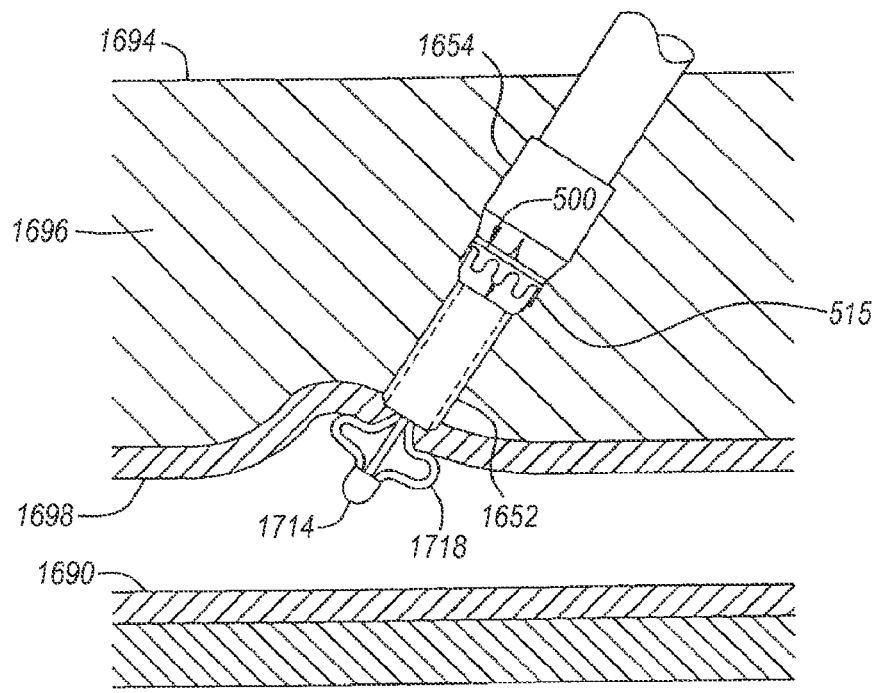

As shown in FIG. 17C, the sheath 1652 can be partially withdrawn from the vessel 1890, until the expandable elements 1718 contact the wall 1898 of the vessel 1890. Thus, the expandable elements 1718 may provide a tactile indication of the position of the sheath 1652 with respect to the wall 1898 of the vessel 1890. In addition, the expandable elements 1718 may assist in "presenting" the wall 1898 of the vessel 1890, e.g., for receiving the closure device 500.

Generally, the closure device 500 can be carried by the carrier assembly 1654 before the first procedure. The closure device 500 can be constrained in its pre-deployed configuration on the carrier assembly 1654, and the carrier assembly 1654 can be provided on and/or adjacent to the proximal end of the sheath 1652. Because the tissue-engaging portions, which may include primary and secondary tissue-engaging portions 515*a*, 515*b* can be biased towards one another, the tissue-engaging portions 314, 316 may slidably contact an inner surface (not shown) of the carrier assembly 1654 or an outer surface of the sheath 1652, thereby constraining the closure device 500 in its pre-deployed configuration.

Figure 17D:
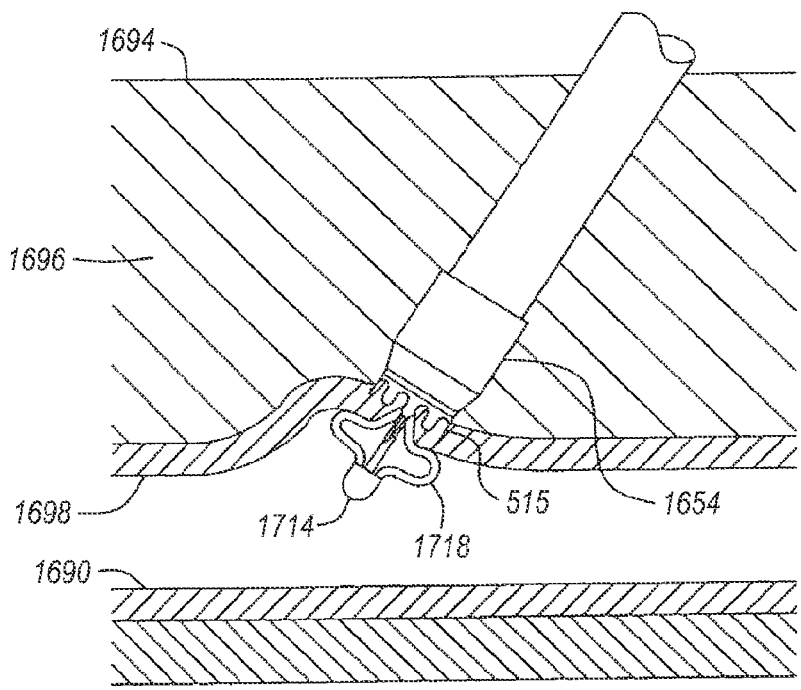

Turning to FIG. 17D, with the sheath 1652 properly positioned, the carrier assembly 1654 may then be actuated, for example, to advance the carrier assembly 1654 distally over the sheath 1652 to deliver the closure device 500. The carrier assembly 1654 may only be advanced a predetermined fixed distance relative to the distal end of the sheath 1652, and consequently, the expandable elements 1718 of the obturator 1700, such that the closure device 500 may substantially engage the wall 1898 of the blood vessel 1890. This predetermined distance may facilitate properly deploying the closure device 100 with respect to the wall 1898 of the vessel 1890, e.g., to prevent advancing the closure device 500 too far, i.e., into the vessel 1890.

As the closure device 500 is deployed from the carrier assembly 1654, the closure device 500 can be expanded to an enlarged diameter, as described, for example, in connection with FIGS. 5A-5E. In the present example, a distal end of the carrier assembly 1654 may include a ramped region (not shown) that may deflect the tissue-engaging portions 515*a*, 515*b* and/or the body of the closure device 100 radially outwardly. As the closure device 100 is advanced over the ramped region, the tissue-engaging portions 515*a*, 515*b* can be deflected radially outwardly as they are being driven into the surrounding tissue, thereby engaging a larger region of tissue than if the tissue-engaging portions 515*a*, 515*b* had been maintained substantially axially.

Alternatively, the closure device 500 may include expandable elements and/or spring elements (not shown), such as those described above, that may facilitate expanding the closure device 500 as it is deployed from the carrier assembly 1654 and/or the sheath 1652. For example, the expandable elements of the closure device 500 can be compressed when the closure device 500 is loaded into the carrier assembly 1654, e.g., thereby allowing a relatively smaller profile carrier assembly 1654 to be used. The closure device 500 may automatically expand upon deployment from the carrier assembly 1654 to engage a larger region of tissue surrounding the opening, such as an arteriotomy 1891 in the wall 1898 of the vessel 1890 (see FIG. 18A).

Figure 18A:
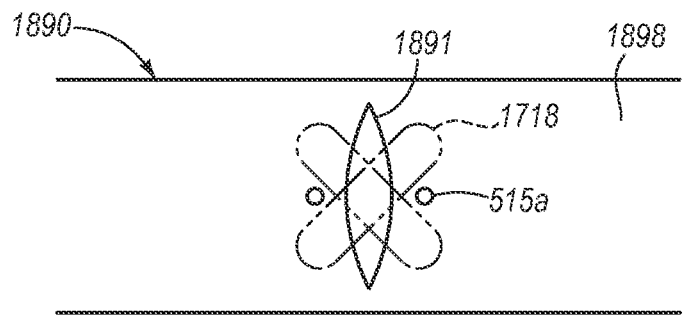
FIG. 18A is a top view of the blood vessel of FIGS. 17A-17F, showing the orientation of the expandable elements of an obturator and openings produced by primary tines of a closure device through tissue relative to an arteriotomy in the vessel.
Figure 18B:
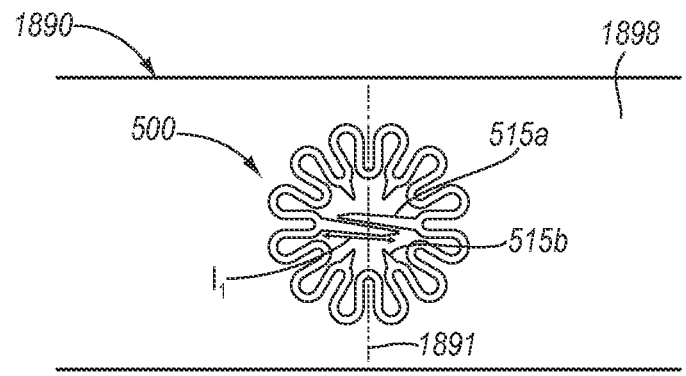
FIG. 18B is a top view of the blood vessel of FIG. 18A, showing the arteriotomy being closed by the closure device through tissue.
Figure 18C:
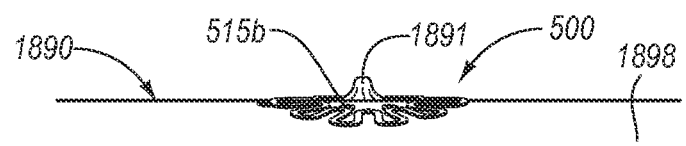
FIG. 18C is a side view of the blood vessel of FIG. 18B, showing the arteriotomy being closed by the closure device.

Once the closure device 500 is deployed entirely or otherwise released from the sheath 1652, the closure device 500 may resiliently move towards its deployed configuration. Although the length, $l_1$, in FIG. 18B is illustrated as extending from a curved region (not shown), beyond the central device axis (not shown), it can be possible for the length, $l_1$, to be less than this distance, such as a length defined from a curved region to the central device axis or a length defined from a curved region toward, but not passing the central axis, as discussed previously.

During delivery of the closure device 500, radiopaque markers (not shown) on the closure device 500, the carrier assembly 1654, and/or the expandable members 1718 can be monitored, e.g., using fluoroscopy, to facilitate observing and/or positioning the apparatus 1600. Thus, a relative position of the closure device 500 with respect to the expandable elements 1718, and consequently to the wall 1898 of the vessel 1890, can be ascertained before the closure device 100 is deployed from the carrier assembly 1654. Markings may also assist in locating a deployed closure device 500.

Turning to FIGS. 17A and 17B, in some examples, the expandable members 1718 of the obturator 1700 can be rotationally offset from the one or more tissue-engaging portions 515*a*, 515*b* on the closure device 500. For example, if the closure device 500 includes primary tissue-engaging portions 515*a* (such as those shown in FIGS. 5A-5E), the obturator 1700 and closure device 500 may have a predetermined relative angular orientation about the central device axis 510. In the present example, the closure device 500 can be loaded onto the carrier assembly 1754 in a predetermined angular orientation and the obturator 1700 can be receivable in the sheath 1752 only in a predetermined angular orientation that is offset such that the tissue-engaging portions 515*a*, 515*b* are out of axial alignment with the expandable elements 1718, as shown in FIG. 18A.

This predetermined rotational orientation may substantially minimize the possibility of the primary tissue-engaging portions 515*a* contacting and/or damaging the expandable elements 1718. For example, with particular reference to FIG. 18A, a relative angular orientation of the closure device 500 and obturator 1700 is shown relative to an arteriotomy 1891 in the wall 1898 of the vessel 1890. Here, the expandable elements 1718 can be oriented to crisscross diagonally the arteriotomy 1891 within the interior of the vessel 1890. Because of the natural structure of the tissue in the wall of a vessel, an arteriotomy generally tends to adopt an elongate shape that extends transversely to the direction of flow (i.e., across the circumference of the vessel wall).

The primary tissue-engaging portions 515*a* can be oriented such that the primary tissue-engaging portions 515*a* pierce and/or engage the wall 1898 of the vessel 1890 on either side of the arteriotomy 1891, as shown. With the expandable elements 1718 crisscrossing diagonally, risk of contact with the primary tissue-engaging portions 515*a* can be substantially reduced. Thus, in some examples, the primary tissue-engaging portions 515*a* can be sufficiently long to extend entirely through the wall 1898 of the vessel 1890 while avoiding the expandable elements 1718.

The expandable elements 1718 may then be collapsed and/or withdrawn into the distal end 1664 of the sheath 1652. As the closure device 500 is released entirely from the sheath 1652, the primary tissue-engaging portions 515*a* may partially overlap, as shown in FIG. 5A, thereby pulling the arteriotomy 1891 closed, similar to a single-thread suture. For example, the expandable elements 1718 can be automatically collapsed immediately before or after the closure device 500 is deployed from the carrier assembly 1654 or when the carrier assembly 1654 reaches its extreme distal position. In the present example, the distal portion 1715*b* of the obturator 1700 can be collapsed and retracted into the sheath 1654 after the primary and/or secondary tissue-engaging portions 515*a*, 515*b* have pierced and/or engaged the wall 1898 of the vessel 1890, but before the closure device 500 is entirely released from the sheath 1652.

In addition, if the closure device 500 includes secondary tissue-engaging portions 515*b* (such as those shown in FIG. 18B), the secondary tissue-engaging portions 515*b* may penetrate (partially in the present example) and/or engage the wall 1898 of the vessel 1890 during deployment of the closure device 500. In the present example, the lengths of the secondary tissue-engaging portions 515*b* can be relatively short or stop members (not shown) can be provided that may prevent the primary and/or secondary tissue-engaging portions 515*a*, 515*b* from piercing entirely through the wall 1898. When the closure device 500 is released, the primary and/or secondary tissue-engaging portions 515*a*, 515*b* may pull the tissue inwardly, behaving somewhat similarly to a purse-string suture, to enhance closing the arteriotomy 1891.

Once the closure device 500 is successfully deployed into the wall 1898 of the vessel 1890, e.g., on either side of an arteriotomy 1891, the apparatus 1600 can be withdrawn from the passage 1692. The entire apparatus 1600 can be removed in one step, or alternatively, the obturator 1700 may first be withdrawn from the sheath 1652 before withdrawing the sheath 1652, thereby leaving the closure device 500 in place to close the arteriotomy 1891 and/or seal the passage 1692.

In the deployed configuration, the closure device 500 for managing access through tissue may substantially close and/or seal the incision, puncture, or other passage 1692 that extends from a patient's skin 1694, through intervening tissue 1696, and into a wall 1898 of a vessel 1890 or other body lumen; engage tissue in other procedures, e.g., to connect tissue segments together or otherwise to secure tissue structures with respect to one another (i.e. attach an anastomosis during a bypass procedure); and/or close an aperture (i.e. a puncture, cut, tear, and/or other aperture) on the surface of the patient's skin 1694. After the closure device 500 is deployed, it can be desirable to perform a second procedure. The location of the second procedure can be through the closure device 500. For example, it can be desirable to provide access through the tissue and through the closure device 500 for performing a second therapeutic or diagnostic procedure.

Figure 17E:
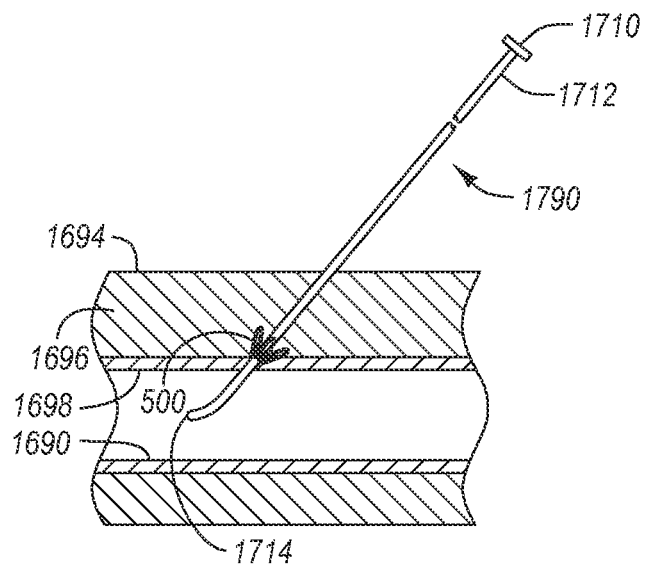

To perform the second procedure, as shown in FIG. 17E, a guide wire 1790, rail, stylet, and/or other device can be inserted into or otherwise positioned within the vessel 1890, i.e., through the closure device 500 for managing access through tissue and/or the passage 1692. Inserting a guide wire 1790 and/or other device may move the closure device 500 for managing access through the tissue from the deployed configuration into another configuration. In the present example, the guide wire 1790 or other device may have a diameter that is larger than the first distance $d_1$ between two tissue-engaging portions 515a, 515b in the deployed configuration but is smaller than the second distance $d_2$ between the two tissue-engaging portions 515a, 515b in the pre-deployed configuration, such that the closure device 100 for managing access through tissue can be moved from the deployed configuration toward the pre-deployed configuration, though may not move to the pre-deployed configuration. In other examples, the guide wire 1790 or other device may have a diameter that is larger than the first distance $d_1$ but substantially the same size as the second distance $d_2$ such that the closure device 500 can be moved from the deployed configuration to the pre-deployed configuration. In further examples, the closure device 500 may move toward and/or to an access configuration, such as the access configuration shown in FIG. 5E. The movement of the closure device 500 for managing access through tissue may depend on the size of the device inserted through the closure device 500 for managing access through tissue, the characteristics of the closure device 500 (i.e. the stiffness in different directions), and/or other factors.

Figure 17F:
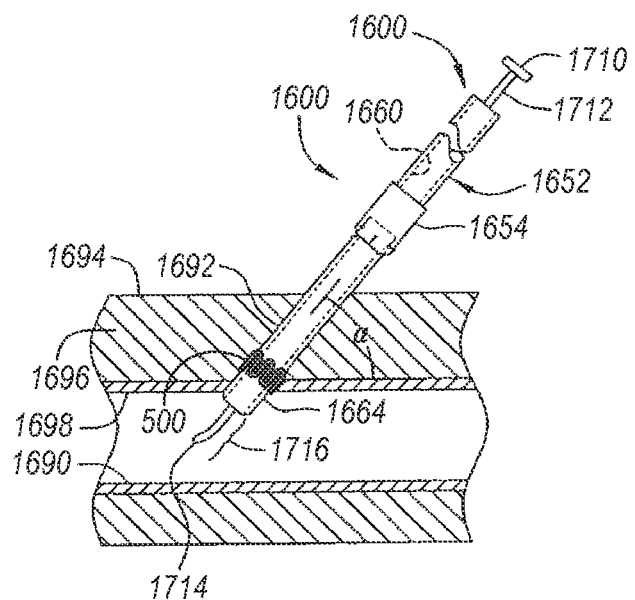

To perform the second procedure, as shown in FIG. 17F, the sheath 1652 can be reinserted into or otherwise positioned within the vessel 1890, i.e., through the closure device 500 for managing access through tissue and/or the passage 1692. The sheath 1652 can be advanced over the guide wire 1790, rail, stylet, and/or other device positioned through the closure device 500 for managing access through tissue and/or passage 1692 into the vessel 1890. As shown in FIG. 17F, the sheath may have a diameter that is larger than a first distance $d_1$ and substantially the same size as a second distance $d_2$, such that the closure device 500 may move from the deployed configuration towards and/or to the pre-deployed configuration.

Embodiments of the closure device and the can expander/removal device, including the expansion members, can include a material made from any of a variety of known suitable materials, such as a shaped memory material (SMM). For example, the SMM can be shaped in a manner that allows for restriction to induce a substantially tubular, linear orientation while within a delivery shaft, but can automatically retain the memory shape of the closure device once extended from the delivery shaft. SMMs have a shape memory effect in which they can be made to remember a particular shape. Once a shape has been remembered, the SMM may be bent out of shape or deformed and then returned to its original shape by unloading from strain or heating. Typically, SMMs can be shape memory alloys (SMA) comprised of metal alloys, or shape memory plastics (SMP) comprised of polymers. The materials can also be referred to as being superelastic.

Usually, an SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and can be tuned by varying the elemental ratios or by the conditions of manufacture.

For example, the primary material of a closure device or the expansion members can be of a NiTi alloy that forms superelastic nitinol. In the present case, nitinol materials can be trained to remember a certain shape, straightened in a shaft, catheter, or other tube, and then released from the catheter or tube to return to its trained shape. Also, additional materials can be added to the nitinol depending on the desired characteristic. The alloy may be utilized having linear elastic properties or non-linear elastic properties.

An SMP is a shape-shifting plastic that can be fashioned into a closure device or expander/removal device, including the expansion members, in accordance with the present invention. Also, it can be beneficial to include at least one layer of an SMA and at least one layer of an SMP to form a multilayered body; however, any appropriate combination of materials can be used to form a multilayered endoprosthesis. When an SMP encounters a temperature above the lowest melting point of the individual polymers, the blend makes a transition to a rubbery state. The elastic modulus can change more than two orders of magnitude across the transition temperature (Ttr). As such, an SMP can formed into a desired shape of a closure device or expander/removal device, including the expansion members, by heating it above the Ttr, fixing the SMP into the new shape, and cooling the material below Ttr. The SMP can then be arranged into a temporary shape by force, and then resume the memory shape once the force has been applied. Examples of SMPs include, but are not limited to, biodegradable polymers, such as oligo(ε-caprolactone) diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

A device or member having at least one layer made of an SMM or suitable superelastic material and other suitable layers can be compressed or restrained in its delivery configuration within a delivery device using a sheath or similar restraint, and then deployed to its desired configuration at a deployment site by removal of the restraint. A device or member made of a thermally-sensitive material can be deployed by exposure of the closure device to a sufficient temperature to facilitate expansion.

Also, the device or member can be comprised of a variety of known suitable deformable materials, including stainless steel, silver, platinum, tantalum, palladium, nickel, titanium, nitinol, nitinol having tertiary materials, niobium-tantalum alloy optionally doped with a tertiary material cobalt-chromium alloys, or other known biocompatible materials. Such biocompatible materials can include a suitable biocompatible polymer in addition to or in place of a suitable metal. A device or member can include biodegradable or bioabsorbable materials, which can be either plastically deformable or capable of being set in the deployed configuration. If plastically deformable, the material can be selected to allow the device or member to be expanded in a similar manner using an expandable member so as to have sufficient radial strength and also to reduce recoil once expanded. If the polymer is to be set in the deployed configuration, the expandable member can be provided with a heat source or infusion ports to provide the required catalyst to set or cure the polymer.

In one embodiment, the closure device or other medical device, including the expander/removal device and/or the expansion members, is made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol closure device or other medical device, including the expander/removal device and/or the expansion members, comparable to that of a stainless steel device or member of the same size and shape coated with a thin layer of gold. The nitinol device or member may have improved radiopacity yet may retain its superelastic and shape memory behavior and further maintains a thin strut/wall thickness for high flexibility. For example, an embodiment of a device or member may have 42.8 atomic percent nickel, 49.7 atomic percent titanium, and 7.5 atomic percent platinum.

In one embodiment, the closure device or other medical device, including the expander/removal device and/or the expansion members, can be made at least in part of a high strength, low modulus metal alloy comprising Niobium, Tantalum, and at least one element selected from the group consisting of Zirconium, Tungsten, and Molybdenum. The medical devices or members according to the present invention may provide superior characteristics with regard to bio-compatibility, radio-opacity and MRI compatibility.

Furthermore, the closure device body or other medical device, including the expander/removal device and/or the expansion members, can be formed from a ceramic material. In one aspect, the ceramic can be a biocompatible ceramic that optionally can be porous. Examples of suitable ceramic materials include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of a closure device or layer thereof.

Moreover, the closure device body or other medical device, including the expander/removal device and/or the expansion members, can include a radiopaque material to increase visibility during placement. Optionally, the radiopaque material can be a layer or coating any portion of the device or member. The radiopaque materials can be platinum, tungsten, silver, stainless steel, gold, tantalum, bismuth, barium sulfate, or a similar material.

It is further contemplated that the external surface and/or internal surface of the devices or members (e.g., exterior and luminal surfaces) as well as the entire body can be coated with another material having a composition different from the primary material. The use of a different material to coat the surfaces can be beneficial for imparting additional properties to the device or member, such as providing radiopaque characteristics, drug-reservoirs, and improved biocompatibility.

In one embodiment, at least one biocompatible polymeric layer can be a coating that is applied over the entire device or member, or to select portions. Examples of such biocompatible polymeric materials can include a suitable hydrogel, hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like. Additionally, the coating can include hydrophilic and/or hydrophobic compounds, polypeptides, proteins, amino acids, polyethylene glycols, parylene, heparin, phosphorylcholine, or the like.

The coatings can also be provided on the device or member to facilitate the loading or delivery of beneficial agents or drugs, such as therapeutic agents, pharmaceuticals and radiation therapies. As such, the material and/or holes can be filled and/or coated with a biodegradable material.

Accordingly, the polymeric coating material can contain a drug or beneficial agent to improve the use of the endoprosthesis or other medical device, including the expander/removal device and/or the expansion members. Such drugs or beneficial agents can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof.

In addition to various medical devices or members, the coatings on these devices or members may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) II b/III a inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), everolimus, azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors. Also, it should be recognized that many active agents have multiple pharmaceutical uses other than those specifically recited.

In one configuration, at least a portion of the external surfaces of the devices or members, such as the closure device, can include a coating comprised of polytetrafluoroethylene (PTFE), expanded PTFE (ePTFE), Dacron, woven materials, cut filaments, porous membranes, harvested vessels and/or arteries, or others such materials to form a stent graft prosthesis. Similarly, a medical device, such as a valve, a flow regulator or monitor device, can be used with the closure device, such that the closure device functions as an anchor for the medical device within the body lumen.

In one configuration, different external surfaces of a device or member, such as a low stress zone less susceptible to flexing, can be coated with functional layers of an imaging compound or radiopaque material. The radiopaque material can be applied as a layer at low stress zones of the device or member. Also, the radiopaque material can be encapsulated within a biocompatible or biodegradable polymer and used as a coating. For example, the suitable radiopaque material can be palladium platinum, tungsten, silver, stainless steel, gold, tantalum, bismuth, barium sulfate, or a similar material. The radiopaque material can be applied as layers on selected surfaces of the device or member using any of a variety of well-known techniques, including cladding, bonding, adhesion, fusion, deposition or the like.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. A method, comprising:
    placing a closure device, having a pre-deployed configuration and a deployed configuration, into proximity with a tissue surface of a body lumen having a puncture defined in a side of the body lumen in the pre-deployed configuration; and
    moving the closure device to the deployed configuration to pull the tissue adjacent the puncture inwardly to close the puncture and close communication with tissue below the tissue surface, wherein the closure device includes a curved interior surface configured to contact the tissue surface, the curved interior surface approximating a curvature of the body lumen adjacent the puncture, wherein the curved interior surface is curved relative to an axis that is perpendicular to a longitudinal axis of the closure device, in the deployed configuration.

2. The method as in claim 1, wherein the tissue is a blood vessel.

3. The method as in claim 1, wherein the tissue is a wall of a body lumen.

4. The method as in claim 1, wherein the closure device further comprises a radiopaque marker and wherein the method further comprises locating the deployed closure device using the radiopaque marker.

5. The method as in claim 1, wherein the closure device comprises a plurality of tines extending towards a central axis of the closure device in the deployed configuration.

6. The method as in claim 5, further comprising deploying a locator through the closure device prior to moving the closure device to the deployed configuration.

7. The method as in claim 6, further comprising retracting the locator through the closure device following moving the closure device to the deployed configuration.

8. The method as in claim 1, wherein the curved interior surface is curved relative to a single axis that is perpendicular to a longitudinal axis of the closure device.

9. The method as in claim 8, wherein the curved interior surface is substantially parallel to a second axis that is perpendicular to a longitudinal axis of the closure device.

10. The method as in claim 1, wherein the closure device is mirrored about a first axis and is curved relative to an orthogonal second axis that is parallel to a longitudinal axis of the body lumen.

11. A method, comprising:
    placing a closure device, in a pre-deployed configuration, into proximity with a tissue surface of a body lumen having a puncture defined in a side of the body lumen, the closure device comprising a body and a plurality of tissue engaging portions;
    moving the closure device to a deployed configuration such that a curved interior surface of the closure device is moved into contact with the tissue surface, the curved interior surface approximating a curvature of the body lumen, the curved interior surface defining a partially cylindrical shape in the deployed configuration;

deploying a locator through the closure device prior to moving the closure device to the deployed configuration and deploying a plurality of expandable elements to provide tactile feedback for locating another tissue surface opposite the tissue surface.

12. The method as in claim 11, wherein moving the closure device to the deployed configuration comprises deploying the closure device from a delivery device and allowing the closure device to move to the deployed configuration, the closure device being biased toward the deployed configuration.

13. The method as in claim 11, moving the closure device to the deployed configuration comprises advancing a carrier assembly distally to deploy the closure device and permit the closure device to move to the deployed configuration, the closure device being biased toward the deployed configuration.

14. The method as in claim 11, further comprising retracting the locator through the closure device following moving the closure device to the deployed configuration.

15. The method as in claim 11, further comprising advancing a medical device through the closure device following moving the closure device to the deployed configuration.

16. A method, comprising:
positioning a delivery sheath in proximity with a tissue surface of a wall of a body lumen having a puncture formed in a side of the body lumen;
placing a closure device, in a pre-deployed configuration, into proximity with the tissue surface of the wall of the body lumen and the puncture, the closure device comprising a body having a concave interior surface and a convex exterior surface and a plurality of tissue engaging portions extending generally parallel to a central axis of the closure device in the pre-deployed configuration, the closure device having the pre-deployed configuration and a deployed configuration; and
moving the closure device to the deployed configuration such that a curved interior surface of the closure device is moved into contact with the tissue surface to pull the tissue adjacent the puncture inwardly to close the puncture and close communication with tissue below the tissue surface, the curved interior surface approximating a curvature of the body lumen adjacent the puncture, a first portion of the curved interior surface being curved relative to a first axis that is perpendicular to a longitudinal axis of the closure device and a second portion of the curved interior surface being curved relative to a second axis that is perpendicular to the first axis, wherein the first portion is curved distally and the second portion is curved proximally.

17. The method as in claim 16, wherein the closure device further comprises a radiopaque marker and wherein the method further comprises locating the deployed closure device using the radiopaque marker.

18. The method as in claim 17, further comprising advancing a medical device through the closure device following locating the closure device using the radiopaque marker and following moving the closure device to the deployed configuration.

19. The method as in claim 16, wherein moving the closure device to the deployed configuration comprises deploying the closure device from the delivery sheath and allowing the closure device to move to the deployed configuration, the closure device being biased toward the deployed configuration.

\* \* \* \* \*